United States Patent
Dai et al.

(10) Patent No.: US 9,189,595 B2
(45) Date of Patent: Nov. 17, 2015

(54) APPARATUS AND ASSOCIATED METHOD FOR ANALYZING SMALL MOLECULE COMPONENTS IN A COMPLEX MIXTURE

(75) Inventors: Hongping Dai, Chapel Hill, NC (US); Corey Donald DeHaven, Raleigh, NC (US)

(73) Assignee: METABOLON INC., Research Triangle Park, NC (US)

(*) Notice: Subject to any disclaimer, the term of this patent is extended or adjusted under 35 U.S.C. 154(b) by 727 days.

(21) Appl. No.: 13/431,126

(22) Filed: Mar. 27, 2012

(65) Prior Publication Data

US 2012/0239306 A1 Sep. 20, 2012

Related U.S. Application Data

(63) Continuation of application No. PCT/US2010/051091, filed on Oct. 1, 2010.

(60) Provisional application No. 61/248,040, filed on Oct. 2, 2009, provisional application No. 61/347,287, filed on May 21, 2010.

(51) Int. Cl.
| | |
|---|---|
| G06F 19/00 | (2011.01) |
| G06F 19/24 | (2011.01) |
| G06K 9/00 | (2006.01) |
| H01J 49/00 | (2006.01) |
| H01J 49/26 | (2006.01) |
| H01J 49/02 | (2006.01) |

(52) U.S. Cl.
CPC .............. *G06F 19/24* (2013.01); *G06F 19/703* (2013.01); *G06F 19/707* (2013.01); *G06K 9/00496* (2013.01); *G06K 9/00523* (2013.01); *H01J 49/0036* (2013.01); *H01J 49/02* (2013.01); *H01J 49/26* (2013.01)

(58) Field of Classification Search
CPC . G06F 19/703; G06F 19/707; G06K 9/00523; G06K 9/00496; H01J 49/0036; H01J 49/02; H01J 49/26
USPC .............. 702/22, 32, 197; 250/282, 287, 288; 436/71; 73/23.36
See application file for complete search history.

(56) References Cited

U.S. PATENT DOCUMENTS

| | | | | |
|---|---|---|---|---|
| 4,315,149 A | * | 2/1982 | Ledford, Jr. ................... | 250/282 |
| 4,353,242 A | * | 10/1982 | Harris et al. ................. | 73/23.36 |
| 5,300,771 A | * | 4/1994 | Labowsky ..................... | 250/282 |
| 6,787,760 B2 | * | 9/2004 | Belov et al. .................... | 250/282 |

(Continued)

*Primary Examiner* — Carol S Tsai
(74) *Attorney, Agent, or Firm* — Womble Carlyle Sandridge & Rice, LLP

(57) ABSTRACT

A method, apparatus, and computer-readable storage medium are provided for analyzing data from a component separation/mass spectrometer (CS-MS), wherein an intensity peak is determined, with an area thereof determined using an integration procedure, in each two-dimensional data set. The intensity peak indicates a sample component, and the area thereof indicates a relative quantity of the sample component. An integration procedure determines the area of selected peaks of a first portion of the two-dimensional data sets associated with a first sample component, and is applied to the intensity peaks of a second portion having the areas thereof not determined by that integration procedure, to adjust the relative quantity of the first sample component in the second portion samples relative to the relative quantity of the first sample component in the first portion samples. The re-integration may also involve determining whether a second sample component is indicated by the intensity peak.

52 Claims, 9 Drawing Sheets

(56) References Cited

U.S. PATENT DOCUMENTS

| | | | |
|---|---|---|---|
| 6,969,763 B1* | 11/2005 | Ecker et al. | 536/24.3 |
| 7,005,255 B2 | 2/2006 | Kaddurah-Daouk et al. | |
| 7,072,773 B2* | 7/2006 | Plumb et al. | 702/32 |
| 7,170,052 B2* | 1/2007 | Furutani et al. | 250/287 |
| 7,329,489 B2 | 2/2008 | Kaddurah-Daouk et al. | |
| 7,418,352 B2* | 8/2008 | Plumb et al. | 702/32 |
| 7,433,787 B2 | 10/2008 | Barrett, Jr. et al. | |
| 7,510,880 B2* | 3/2009 | Gross et al. | 436/71 |
| 7,561,975 B2 | 7/2009 | Young et al. | |
| 8,178,834 B2* | 5/2012 | Gorenstein et al. | 250/282 |
| 8,480,110 B2* | 7/2013 | Gorenstein et al. | 280/282 |
| 8,658,427 B2* | 2/2014 | van Ravenzwaay et al. | 436/71 |
| 8,716,656 B2* | 5/2014 | Peng et al. | 250/288 |
| 8,766,172 B2* | 7/2014 | Gorenstein et al. | 250/282 |
| 2003/0017483 A1* | 1/2003 | Ecker et al. | 435/6 |
| 2003/0071206 A1* | 4/2003 | Belov et al. | 250/282 |
| 2005/0127287 A1* | 6/2005 | Plumb et al. | 250/281 |
| 2005/0230615 A1* | 10/2005 | Furutani et al. | 250/287 |
| 2007/0083337 A1* | 4/2007 | Plumb et al. | 702/32 |
| 2007/0265216 A1* | 11/2007 | Gross et al. | 514/44 |
| 2009/0076737 A1* | 3/2009 | Wang et al. | 702/23 |
| 2009/0093971 A1 | 4/2009 | Barrett, Jr. et al. | |
| 2009/0294645 A1* | 12/2009 | Gorenstein et al. | 250/282 |
| 2012/0259557 A1* | 10/2012 | Gorenstein et al. | 702/32 |
| 2013/0080073 A1* | 3/2013 | de Corral | 702/23 |
| 2014/0025342 A1* | 1/2014 | Gorenstein et al. | 702/197 |

* cited by examiner

FIG. 9

Start

↓ determining a selected ion peak in each of a plurality of two-dimensional data sets, each of the two-dimensional data sets being determined from a respective three-dimensional data set including data obtained from the component separation and mass spectrometer system, for each of a plurality of samples  900

↓ determining an area associated with the selected ion peak, using one of a plurality of integration procedures, for each of the two-dimensional data sets  910

↓ determining an identity of a first sample component associated with the selected ion peaks of the two-dimensional data sets, the area of each selected ion peak associated with the first sample component further corresponding to a relative quantity of the first sample component in the respective sample  920

↓ comparing the selected ion peaks across the plurality of two-dimensional data sets to determine whether a predetermined one of the integration procedures was used to determine the area associated with the first sample component of a first portion of the selected ion peaks of the two-dimensional data sets, the first portion of the selected ion peaks of the two-dimensional data sets indicating a second sample component associated therewith in addition to the first sample component, the predetermined one of the integration procedures used to determine the area of each selected ion peak of the first portion associated with the first sample component comprising a first sample component mask integration procedure  930

↓ determining, if the predetermined one of integration procedures was used to determine the area associated with the first sample component of the first portion of the selected ion peaks, an area of each selected ion peak, corresponding to a relative quantity of the second sample component, for the first portion of the selected ion peaks of the two-dimensional data sets, using a second sample component mask integration procedure  940

↓ applying the first and second sample component mask integration procedures to the selected ion peaks of a second portion of the two-dimensional data sets, the second portion of the two-dimensional data sets previously having the areas of the selected ion peaks thereof determined by one of the integration procedures other than the first sample component mask integration procedure, so as to adjust the relative quantities of the first and second sample components determined to be in the samples corresponding to the second portion of the two-dimensional data sets with respect to the relative quantities of the first and second sample components determined to be in the samples corresponding to the first portion of the two-dimensional data sets  950

↓

End

APPARATUS AND ASSOCIATED METHOD FOR ANALYZING SMALL MOLECULE COMPONENTS IN A COMPLEX MIXTURE

CROSS-REFERENCE TO RELATED APPLICATIONS

This application is a continuation of International Application No. PCT/US2010/051091, filed Oct. 1, 2010, which International Application was published by the International Bureau in English on Apr. 7, 2011, and claims priority to U.S. Provisional Patent Application No. 61/248,040, filed Oct. 2, 2009 and U.S. Provisional Application No. 61/347,287, filed May 21, 2010, and all of which are incorporated herein by reference in their entirety and for all purposes.

BACKGROUND OF THE DISCLOSURE

1. Field of the Disclosure

The present disclosure relates to the field of determining small molecule components in a complex mixture and, more particularly, to an apparatus and associated method for analyzing small molecule components in a complex mixture, with such small molecule analysis including metabolomics, which is the study of small molecules produced by an organism's metabolic processes, or other analysis of small molecules produced through metabolism.

2. Description of Related Art

Metabolomics is the study of the small molecules, or metabolites, contained in a cell, tissue or organ (including fluids) and involved in primary and intermediary metabolism. The term "metabolome" refers to the collection of metabolites present in an organism. The human metabolome encompasses native small molecules (natively biosynthesizeable, non-polymeric compounds) that are participants in general metabolic reactions and that are required for the maintenance, growth and normal function of a cell. Thus, metabolomics is a direct observation of the status of cellular physiology, and may thus be predictive of disease in a given organism. Subtle biochemical changes (including the presence of selected metabolites) are inherent in a given disease. Therefore, the accurate mapping of these changes to known pathways may allow researchers to build a biochemical hypothesis for a disease. Based on this hypothesis, the enzymes and proteins critical to the disease can be uncovered such that disease targets may be identified for treatment with targeted pharmaceutical compounds or other therapy.

Molecular biology techniques for uncovering the biochemical processes underlying disease have been centered on the genome, which consists of the genes that make up DNA, which is transcribed into RNA and then translated to proteins, which then make up the small molecules of the human metabolome. While genomics (study of the DNA-level biochemistry), transcript profiling (study of the RNA-level biochemistry), and proteomics (study of the protein-level biochemistry) are useful for identification of disease pathways, these methods are complicated by the fact that there exist over 25,000 genes, 100,000 to 200,000 RNA transcripts and up to 1,000,000 proteins in human cells. However, it is estimated that there may be as few as 2,500 small molecules in the human metabolome.

Thus, metabolomic technology provides a significant leap beyond genomics, transcript profiling, and/or proteomics. With metabolomics, metabolites and their role in metabolism may be readily identified. In this context, the identification of disease targets may be expedited with greater accuracy relative to other known methods. The collection of metabolomic data for use in identifying disease pathways is generally known in the art, as described generally, for example, in U.S. Pat. Nos. 7,005,255 and 7,329,489 to Metabolon, Inc., each entitled Methods for Drug Discovery, Disease Treatment, and Diagnosis Using Metabolomics. Additional uses for metabolomics data are described therein and include, for example, determining response to a therapeutic agent (i.e., a drug) or other xenobiotics, monitoring drug response, determining drug safety, and drug discovery. However, the collection and sorting of metabolomic data taken from a variety of samples (e.g., from a patient population) consumes large amounts of time and computational power. For example, according to some known metabolomic techniques, spectrometry data for certain samples is collected and plotted in three dimensions and stored in an individual file corresponding to each sample. This data is then, by individual file, compared to data corresponding to a plurality of known metabolites in order to identify known metabolites that may be disease targets. The data may also be used for identification of toxic agents and/or drug metabolites. Furthermore such data may also be used to monitor the effects of xenobiotics and/or used to monitor/measure/identify the xenobiotics and associated metabolites produced by processing (metabolizing) the xenobiotics. However, such conventional "file-based" methods (referring to the individual data file generated for each sample) require the use of large amounts of computing power and memory capacity to handle the screening of large numbers of known metabolites. Furthermore, "file-based" data handling may not lend itself to the compilation of sample population data across a number of samples because, according to known metabolomic data handling techniques, each sample is analyzed independently, without taking into account subtle changes in metabolite composition that may be more readily detectable across a sample population. Furthermore, existing "file-based" method may have other limitations including: limited security and auditability; and poor data set consistency across multiple file copies. In addition, individual files may not support multiple indices (i.e., day collected, sample ID, control vs. treated, drug dose, etc) such that all files must be scanned when only a particular subset is desired.

These limitations in current metabolomic data analysis techniques may lead to the discarding of potentially relevant and/or valuable metabolomic data that may be used to identify and classify particular metabolites as disease targets. Specifically, spectrometry data corresponding to a number of samples (such as tissue samples from individual human subjects) generally results in a large data file corresponding to each sample, wherein each data file must then be subjected to an individual screening process with respect to a library of known metabolites. However, conventional systems do not readily allow for the consolidation of spectrometry data from a number of samples for the subjective evaluation of the data generated by the spectrometry processes. Thus, while a single file corresponding to an individual sample may be inconclusive, such data may be more telling if viewed subjectively in a succinct format with respect to other samples within a sample population.

One particular example of a limitation in current metabolomic data analysis techniques involves the identification and quantification of a metabolite in each of a plurality of sample. In some instances, the identification of the metabolite involves analyzing the data file of each sample to determine whether an indicia (i.e., an intensity peak for a particular mass component, observed at a particular retention time) of that metabolite exists within the respective data files. If such an indicia is determined, quantification of that metabolite may then involve the integration of the area represented by that indicia (i.e., the area under the intensity peak). However, as previously noted, it may be difficult in "file based" data handling methods to verify whether the determined indicia is consistent across samples. For example, it may be difficult to determine whether the identified intensity peaks are aligned with respect to retention time across the samples. Further, there may be instances where the indicia (i.e., the intensity peak) is not clearly defined within the data file of one or more samples. In those instances, the integration procedure used to calculate the area represented by the indicia may vary, for instance, based on the assumptions used or estimates performed in connection with the calculation, particularly where the origin and the terminus of a particular intensity peak is not clearly evident. There may also be instances where the indicia (i.e., the intensity peak) may actually reflect the presence of more than one sample component and, as such, any analysis of those intensity peaks as a whole may be significantly inaccurate. As such, the various assumptions and estimates, which may be difficult to analyze for individual samples when using a file-base data handling method, may result in an inaccurate indication of the quantity of that metabolite (or a plurality of metabolites) present over the plurality of the sample. In this regard, such a quantitative inaccuracy introduced into a metabolomics analysis at such an early stage may lead to larger inaccuracies in subsequent steps or analyses.

Therefore, there exists a need for an improved apparatus and method for solving the technical issues outlined above that are associated with conventional metabolomic data analysis systems. More particularly, there exists a need for an apparatus and method capable of analyzing spectrometry data across samples, with the option of, but not the need for, generating a separate data file for each sample. There also exists a need for an apparatus and method capable of allowing a user to subjectively evaluate spectrometry data across a plurality of samples to identify selected metabolites, for allowing the user to verify or otherwise determine the confidence in the identification of the selected metabolites, for allowing the user to examine the data associated with the identification of the selected metabolites, for example, for sorting, grouping, and/or aligning purposes, and for allowing the user to determine additional information related to the identified selected metabolites, for instance, for quality control and consistency verification purposes. There also exists a need for an improved apparatus and method capable of more accurately identifying and quantifying sample components across samples from the acquired spectrometry data.

BRIEF SUMMARY OF THE DISCLOSURE

The above and other needs are met by aspects of the present disclosure which, in one aspect, provides a first method of analyzing data obtained from a component separation and mass spectrometer system. Such a method comprises determining a selected intensity peak in each of a plurality of two-dimensional data sets, wherein each of the two-dimensional data sets is determined from a respective three-dimensional data set including data obtained from the component separation and mass spectrometer system, for each of a plurality of samples. An area associated with the selected intensity peak is then determined, using one of a plurality of integration procedures, for each of the two-dimensional data sets. An identity of a first sample component associated with the selected intensity peaks of the two-dimensional data sets is then determined, wherein the area of each selected intensity peak associated with the first sample component further corresponds to a relative quantity of the first sample component in the respective sample. The selected intensity peaks are then compared across the plurality of two-dimensional data sets to determine whether a predetermined one of the integration procedures was used to determine the area associated with the first sample component of a first portion of the selected intensity peaks of the two-dimensional data sets, wherein the first portion of the selected intensity peaks of the two-dimensional data sets indicate a second sample component associated therewith in addition to the first sample component. The predetermined one of the integration procedures used to determine the area of each selected intensity peak of the first portion associated with the first sample component further comprises a first sample component mask integration procedure. If the predetermined one of integration procedures was used to determine the area associated with the first sample component of the first portion of the selected intensity peaks, an area of each selected intensity peak, corresponding to a relative quantity of the second sample component, is then determined for the first portion of the selected intensity peaks of the two-dimensional data sets, using a second sample component mask integration procedure. The first and second sample component mask integration procedures are then applied to the selected intensity peaks of a second portion of the two-dimensional data sets, wherein the second portion of the two-dimensional data sets previously had the areas of the selected intensity peaks thereof determined by one of the integration procedures other than the first sample component mask integration procedure, so as to adjust the relative quantities of the first and second sample components determined to be in the samples corresponding to the second portion of the two-dimensional data sets with respect to the relative quantities of the first and second sample components determined to be in the samples corresponding to the first portion of the two-dimensional data sets.

Another aspect of the present disclosure provides a first apparatus for analyzing data obtained from a component separation and mass spectrometer system, the apparatus comprising a processor and a memory storing executable instructions that, in response to execution by the processor, cause the apparatus to at least perform the steps of the first method aspect of the present disclosure.

A further aspect of the present disclosure provides a first computer-readable storage medium having computer-readable program code portions stored therein that, in response to execution by a processor, cause an apparatus to at least perform the steps of the first method aspect of the present disclosure.

Yet another aspect of the present disclosure provides a second method of analyzing data obtained from a component separation and mass spectrometer system. Such a method comprises determining a selected ion peak in each of a plurality of two-dimensional data sets including data obtained from the component separation and mass spectrometer system, wherein each of the two-dimensional data sets is determined from a respective three-dimensional data set, including the data obtained from the component separation and mass spectrometer system, for each of a plurality of samples. An area associated with the selected ion peak is determined, using one of a plurality of integration procedures, for each of the two-dimensional data sets. A sample component associated with the selected ion peaks of the two-dimensional data sets is then determined, wherein the area associated with each selected ion peak further corresponds to a relative quantity of the sample component in the respective sample. The selected ion peaks are compared across the plurality of two-dimensional data sets to determine the one of the integration procedures used to determine the area of the selected ion peak for a first portion of the two-dimensional data sets, wherein the determined one of the integration procedures comprises a template integration procedure. The template integration procedure is applied to the selected ion peaks of a second portion of the two-dimensional data sets, wherein the second portion of the two-dimensional data sets previously have the areas of the selected ion peaks thereof determined by one of the integration procedures other than the template integration procedure, to adjust the relative quantity of the sample component determined to be in the samples corresponding to the second portion of the two-dimensional data sets with respect to the relative quantity of the sample component determined to be in the samples corresponding to the first portion of the two-dimensional data sets.

Another aspect of the present disclosure provides a second apparatus for analyzing data obtained from a component separation and mass spectrometer system, the apparatus comprising a processor and a memory storing executable instructions that, in response to execution by the processor, cause the apparatus to at least perform the steps of the second method aspect of the present disclosure.

A further aspect of the present disclosure provides a second computer-readable storage medium having computer-readable program code portions stored therein that, in response to execution by a processor, cause an apparatus to at least perform the steps of the second method aspect of the present disclosure.

Thus, the apparatuses and methods for analyzing data obtained from a component separation and mass spectrometer system according to aspects of the present disclosure provide these and other advantages, as detailed further herein. Importantly, these advantages include a compact format that spans a "fourth dimension" across a population of samples, thereby providing increased quality and consistency of analysis results. These advantages also include the capability of identifying additional sample components and the improved capability of determining the relative quantity of one or more of such sample components indicated by the recited intensity peaks.

BRIEF DESCRIPTION OF THE SEVERAL VIEWS OF THE DRAWINGS

Figure 1:
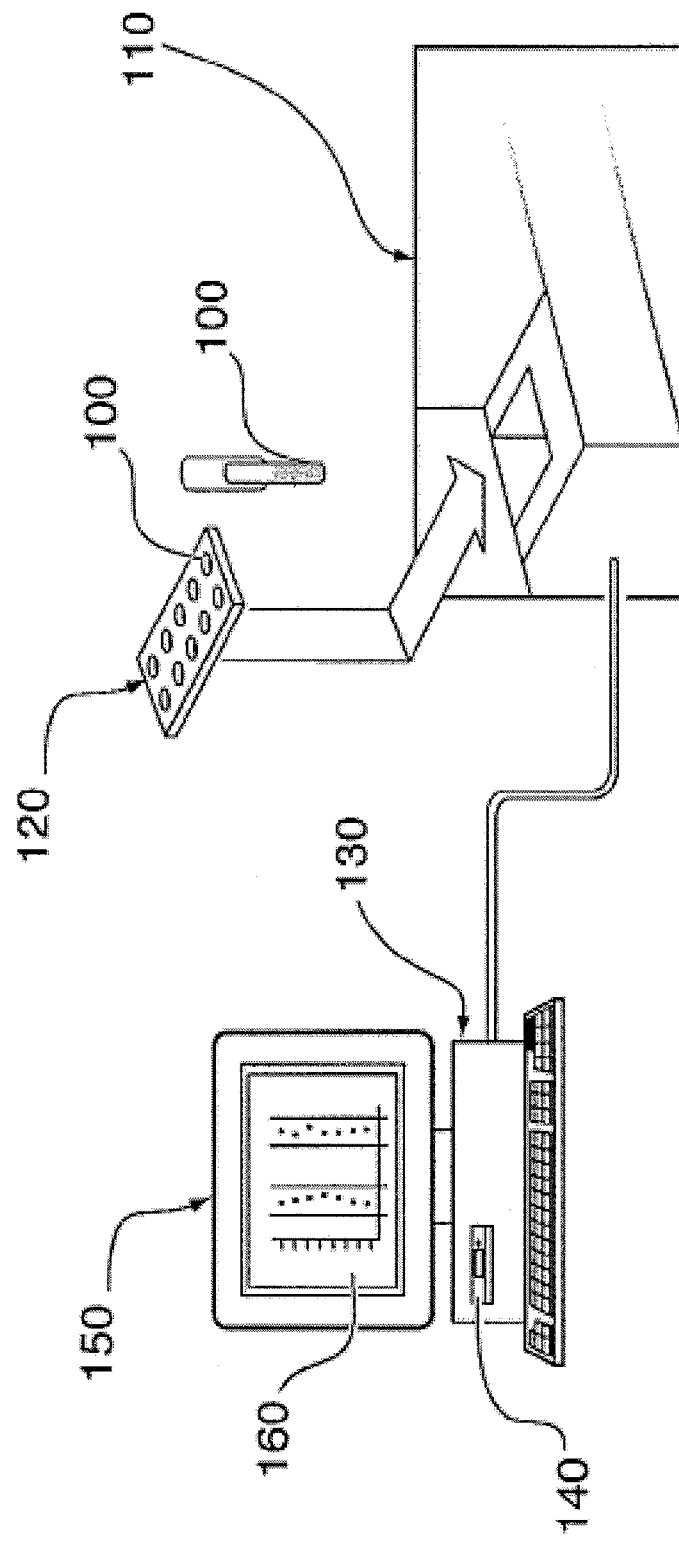
Figure 2:
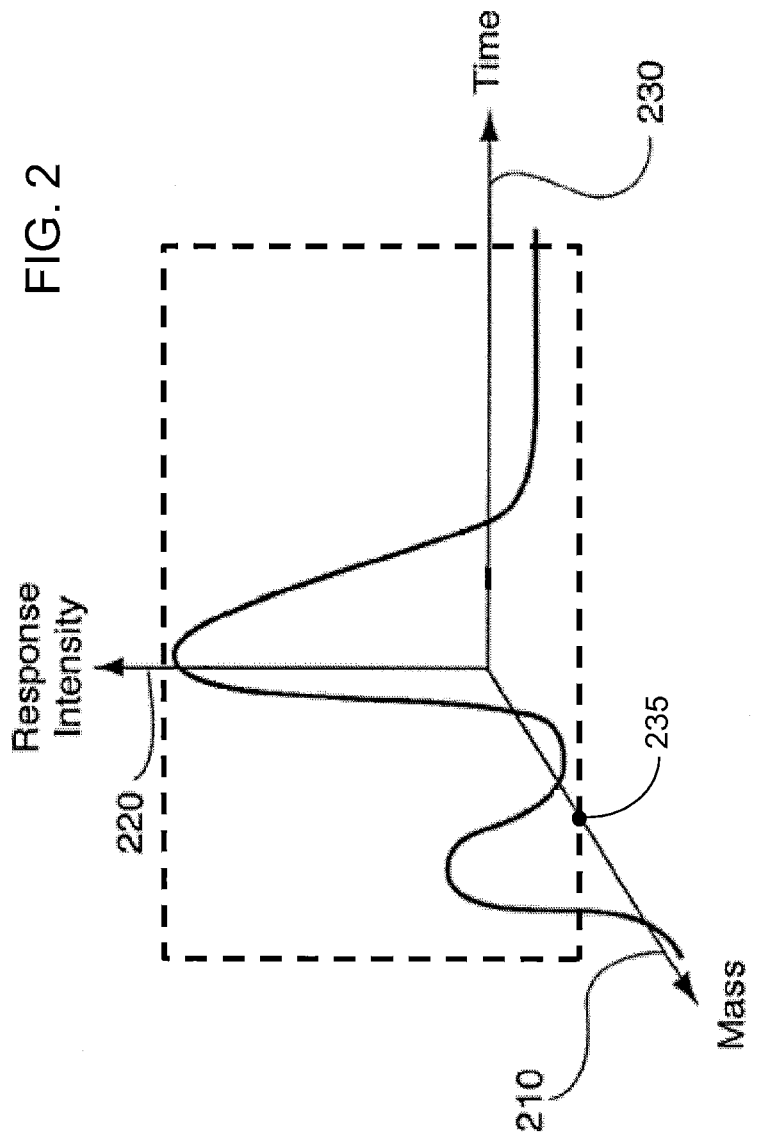
Figure 3:
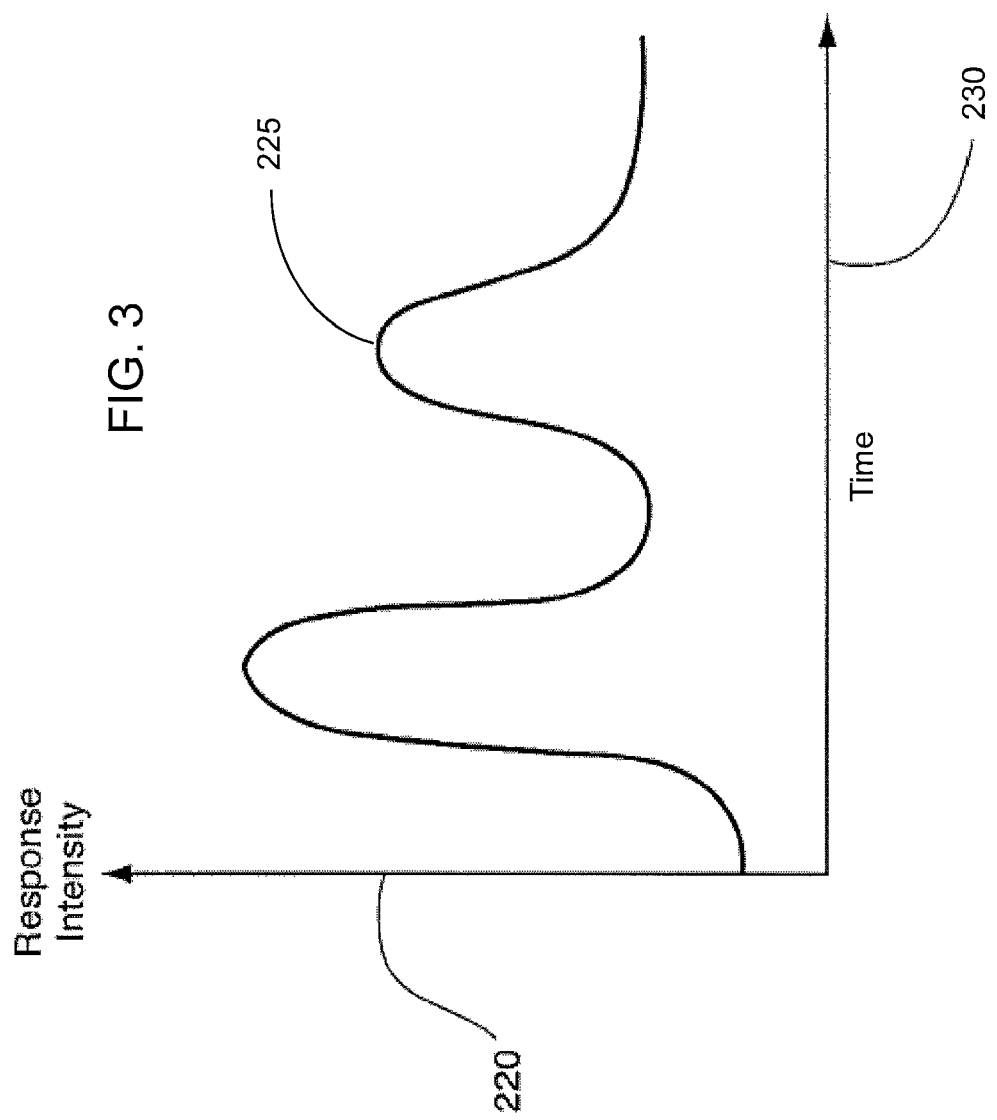
Figure 4:
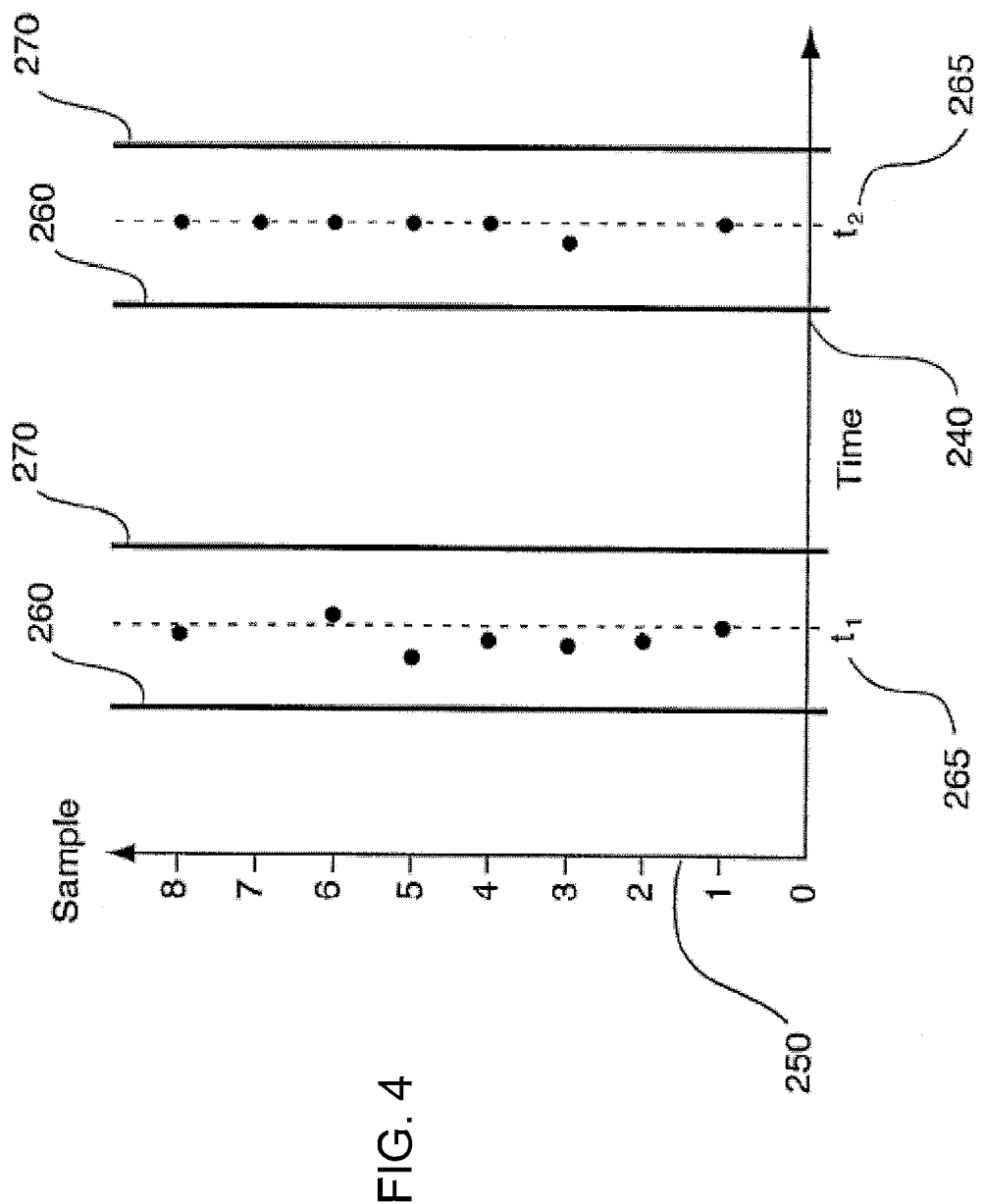
Figure 5:
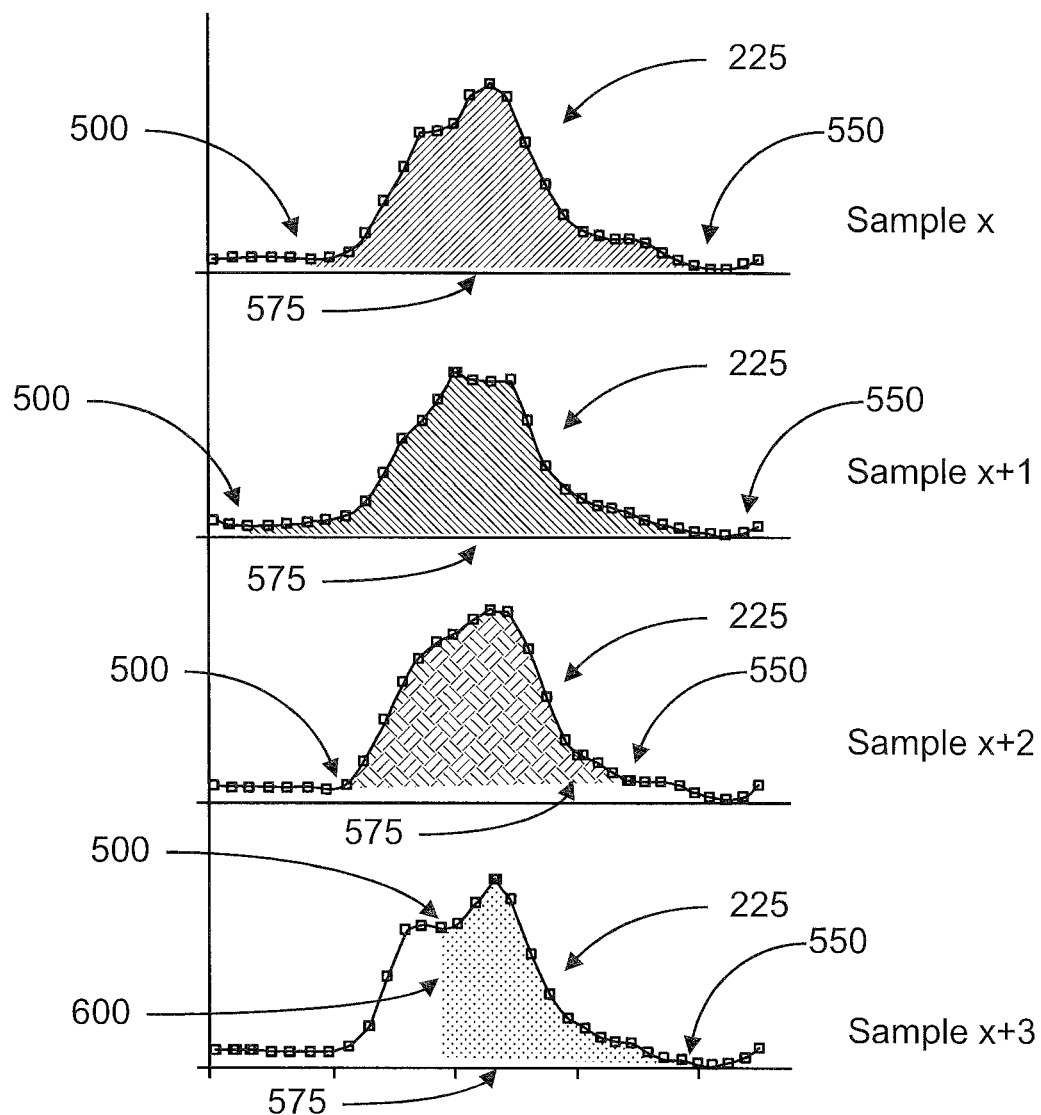
Figure 6A:
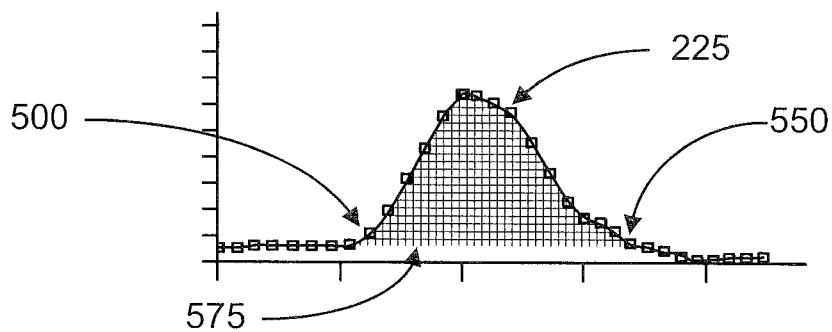
Figure 6B:
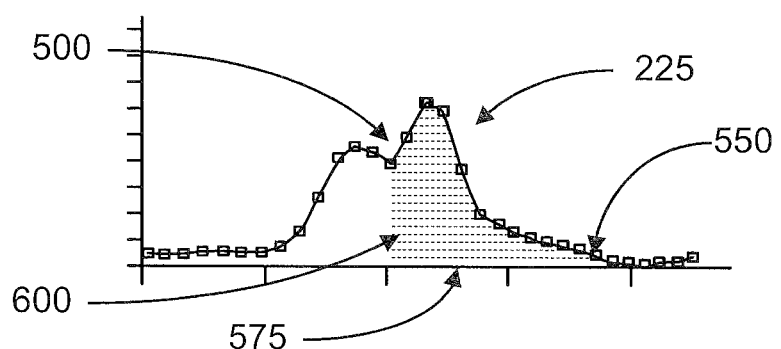
Figure 6C:
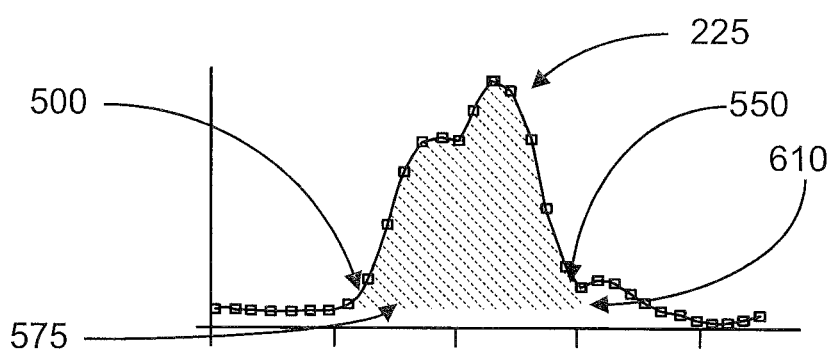
Figure 7:
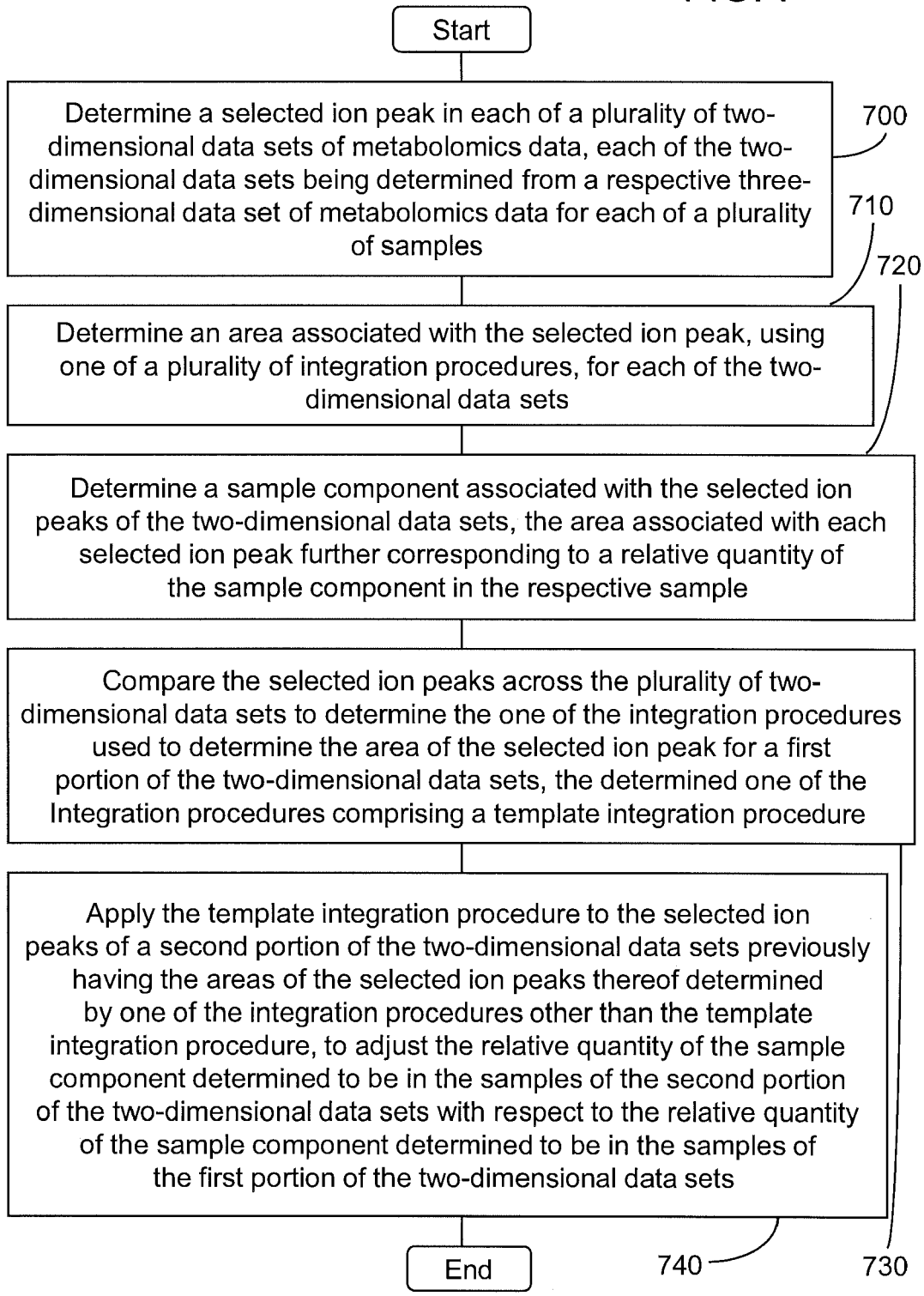
Figure 8:
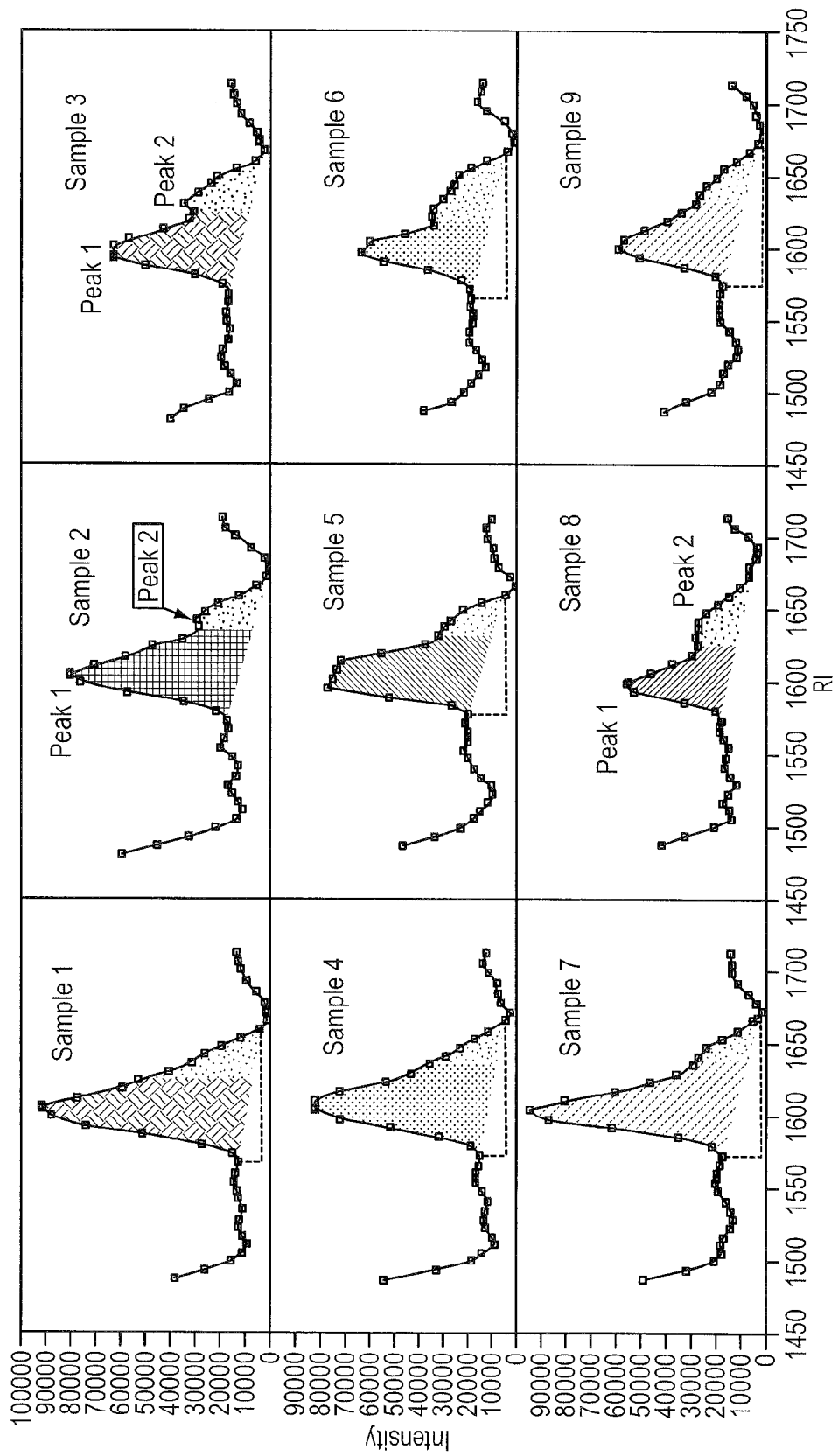

Having thus described the disclosure in general terms, reference will now be made to the accompanying drawings, which are not necessarily drawn to scale, and wherein:

FIG. 1 illustrates a system according to one aspect of the present disclosure including a memory device having a database, a processor device, and a user interface, in communication with a spectrometry device;

FIG. 2 is an illustration of a three-dimensional plot of spectrometry data associated with one exemplary sample;

FIG. 3 is an illustration of a two-dimensional plot for one exemplary sample that may be determined according to some aspects of the present disclosure, and that may be comparable to a similar two-dimensional plot for another exemplary sample, across a plurality of samples;

FIG. 4 is an illustration of a plot that may be generated by some aspects of the present disclosure showing a comparison of selected intensity peaks across a plurality of samples;

FIG. 5 is an illustration of another plot that may be generated by some aspects of the present disclosure showing a comparison of selected intensity peaks across a plurality of samples, which may also be indicative of the alignment of a selected intensity peak between two-dimensional data sets associated therewith;

FIGS. 6a-6c illustrate various plots of a selected intensity peak for different two-dimensional data sets generated by some aspects of the present disclosure, also indicating conditions which may require different integration procedures to determine the areas thereof;

FIG. 7 is an illustration of an operational flow of the apparatuses, methods, and computer program products of one exemplary aspect of the present disclosure;

FIG. 8 illustrates various plots of a selected intensity peak for different two-dimensional data sets representing different samples generated by some aspects of the present disclosure, indicating both an initial integrations for the intensity peaks, in addition to subsequent re-integrations for the intensity peaks indicating the presence and relative quantity of a second sample component, attributed to a shoulder or secondary peak, in addition to the first sample component; and FIG. 9 is an illustration of an operational flow of the apparatuses, methods, and computer program products of another exemplary aspect of the present disclosure.

DETAILED DESCRIPTION OF THE DISCLOSURE

The present disclosure now will be described more fully hereinafter with reference to the accompanying drawings, in which some, but not all aspects of the disclosure are shown. Indeed, this disclosure may be embodied in many different forms and should not be construed as limited to the aspects set forth herein; rather, these aspects are provided so that this disclosure will satisfy applicable legal requirements. Like numbers refer to like elements throughout.

The various aspects of the present disclosure mentioned above, as well as many other aspects of the disclosure, are described in further detail herein. The apparatuses and methods associated with aspects of the present disclosure are exemplarily disclosed, in some instances, in conjunction with an appropriate analytical device which may, in some instances, comprise a separator portion (i.e., a chromatograph) and/or a detector portion (i.e., a spectrometer). One skilled in the art will appreciate, however, that such disclosure is for exemplary purposes only to illustrate the implementation of various aspects of the present disclosure. Particularly, the apparatuses and methods associated with aspects of the present disclosure can be adapted to any number of processes that are used to generate complex sets of data across a plurality of samples, whether biological, chemical, or biochemical, in nature. For example, aspects of the present disclosure may be used with a variety of different analytical devices and processes including, but not limited to: analytical devices including a separator portion (or "component separator" portion) comprising one of a liquid chromatograph (LC) and a gas chromatograph (GC); a cooperating detector portion (or "mass spectrometer" portion) comprising one of a nuclear magnetic resonance imaging (NMR) device; a mass spectrometer (MS); and an electrochemical array (EC); and/or combinations thereof. In this regard, one skilled in the art will appreciate that the aspects of the present disclosure as disclosed herein are not limited to metabolomics analysis. For example, the aspects of the present disclosure as disclosed herein can be implemented in other applications where there is a need to characterize or analyze small molecules present within a sample or complex mixture, regardless of the origin of the sample or complex mixture. For instance, the aspects of the present disclosure as disclosed herein can also be implemented in a bioprocess optimization procedure where the goal is to grow cells to produce drugs or additives, or in a drug metabolite profiling procedure where the goal is to identify all metabolites that are the result of biotranformations of an administered xenobiotic. As will be appreciated by one skilled in the art, these exemplary applications may be very different from a metabolomics analysis, where the goal is only to examine endogenous metabolites. Some other non-limiting examples of other applications could include a quality assurance procedure for consumer product manufacturing where the goal may be to objectively ensure that desired product characteristics are met, in procedures where a large number of sample components can give rise to a particular attribute, such as taste or flavor (e.g., cheese, wine or beer), or scent/smell (e.g., fragrances). One common theme thus exhibited by the aspects of the present disclosure as disclosed herein is that the small molecules in the sample can be analyzed using the various apparatus and method aspects disclosed herein.

FIG. 1 illustrates an example of a system according to one aspect of the present disclosure wherein the system is in communication with an analytical device 110, such as a combination chromatograph (component separator)/mass spectrometer. One skilled in the art will appreciate, however, that the configurations of an analytical device 110 presented herein are for exemplary purposes only, and are not intended to be limiting with respect to the scope of suitable and appropriate analytical devices that may also be applied under the principles disclosed herein As shown, a sample (whether biological, chemical, or biochemical, in nature) 100 may be introduced into the separator portion of the analytical device 110 and analyzed using appropriate techniques, as applied through the detector portion, that will be appreciated by those skilled in the art. For example, the components of a particular sample 100 may pass through a column associated with the separator portion, at different rates and exhibit different spectral responses via the detector portion based upon their specific characteristics. As will be appreciated by one skilled in the art, the analytical device 110 may generate a three-dimensional set of spectrometry data corresponding to each sample 100, wherein the data included in the three-dimensional data set generally indicates the composition of the sample 100. However, such data must first be appropriately analyzed in order to determine the sample composition.

An example of such a three-dimensional set of spectrometry data is shown generally in FIG. 2, and may be plotted on a three-axis plot, including axes for a response intensity 220, a sample component mass element 210, and a time element 230 (particularly, in this example, the retention time or the time that a particular component spends in the column of the separator portion of the analytical device 110). The location of data points in relation to the sample component mass axis 210 may be indicative, for example, of the number of individual component molecules within the sample 100 and the relative mass values for such sample components. According to other aspects of the present disclosure, other analytical devices may be used to generate a three-dimensional set of analytical data corresponding to the sample 100. For example, the analytical device may include, but is not limited to: various combinations of a separator portion comprising one of a liquid chromatograph (LC) (positive or negative channel) and a gas chromatograph (GC); and a cooperating detector portion comprising one of a nuclear magnetic resonance imaging (NMR) device; a mass spectrometer (MS); and an electrochemical array (EC). One skilled in the art will appreciate that such complex three-dimensional data sets may be generated by other appropriate analytical devices that may be in communication with components of aspects of the present disclosure as described in further detail below.

A plurality of samples 100 may be taken individually from a well plate 120 and/or from other types of sample containers and introduced individually into the analytical device 110 for analysis and generation of the corresponding three-dimensional data set (see, e.g., FIG. 2). For example, individual samples 100 may be transferred from a well plate 120 to the analytical device 110 via pipette, syringe, microfluidic passageways defined by a test array, and/or other systems for transferring samples in a laboratory environment. As disclosed herein, the nature of the samples may vary considerably, generally comprising mixtures or complex mixtures including small molecules, wherein such samples may exemplarily include, but are not limited to: blood samples, urine samples, cell cultures, saliva samples, plant tissue and organs (e.g., leaves, roots, stems, flowers, etc), plant extracts, culture media, membranes, cellular compartments/organelles, cerebral spinal fluid (CSF), milk, soda products, food products (e.g., yoghurt, chocolate, juice), and/or other types of biological, chemical, and/or biochemical samples in which the metabolites and/or chemical/molecular components of interest may be present.

As shown in FIG. 1, aspects of the present disclosure may comprise a database (e.g., a relational database) stored at least in part, for example, as executable instructions in a memory or memory device 140 (i.e., a computer-readable storage medium having computer-readable program code portions stored therein), wherein the memory device 140 is in communication with a processor device 130 (e.g., a computer device) for selectively executing the instructions/computer-readable program code portions in the memory device 140 to cause an apparatus to perform particular method steps and/or functions. In some instances, the memory device 140 and/or the processor device 130 may be configured to be in communication with the analytical device 110 for automatically receiving a three-dimensional data set, corresponding to each of the plurality of samples 100, therefrom. The processor device 130 may be in communication with the analytical device 110 via wire line (RS-232, and/or other types of wire connection) and/or wireless (such as, for example, RF, IR, or other wireless communication) techniques such that the database associated with the memory device 140/processor device 130 (and/or in communication therewith) may receive the data set from the analytical device 110 so as to be stored thereby Furthermore, the analytical device 110 may be in communication with one or more processor devices 130 (and associated user interfaces 150) via a wire line and/or wireless computer network including, but not limited to: the Internet, local area networks (LAN), wide area networks (WAN), or other networking types and/or techniques that will be appreciated by one skilled in the art. The database may be structured using commercially-available software, such as, for example, Oracle, Sybase, DB2, or other database software. As shown in FIG. 1, the processor device 130 may be in communication with the memory device 140 (such as a hard drive, memory chip, flash memory, RAM module, ROM module, and/or other memory device 140) for storing/administering the database, including the three-dimensional data sets automatically received from the analytical device 110. In addition, the memory device 140 may also be used to store other received data in the database and/or data otherwise manipulated by the processor device 130.

The processor device 130 may, in some aspects, be capable of converting each of the three dimensional data sets (see FIG. 2) received by the memory device 140 into at least one corresponding two-dimensional data set (see FIG. 3), wherein the at least one two-dimensional data set comprises, for example, a two-dimensional component "profile" of a particular sample 100 at a particular point 235 along one of the three axes, such as the sample component mass axis 210 (wherein the resulting profile illustrates a particular sample component mass detected as a function of time measured from a zero point, the zero point corresponding to when the sample 100 is injected and/or otherwise introduced into the analytical device 110). For example, the processor device 130 may be configured to produce a sample component (retention) time versus intensity profile of the sample for a given sample component mass point 235 (see FIG. 3, for example). The "x" axis in FIG. 2 (or time axis 230, for example) may further, in some instances, be characterized as a retention index and/or a retention time. Thus, the processor device 130 may be further capable of parsing each of the three-dimensional data sets, for each of the plurality of samples, into one or more individual two-dimensional profiles corresponding to particular sample component mass points (element 235, for example) so as to convert each three-dimensional data set (of FIG. 2, for example) into at least one corresponding two-dimensional data set of a selected sample component (having a profile shown, for example, in FIG. 3) that may further be plotted as an intensity response 220 of the corresponding sample component mass versus a sample component time 230.

According to some aspects, the processor device 130 may be configured to selectively execute the executable instructions/computer-readable program code portions stored by the memory device 140 so as to accomplish the identification and quantification of a selected sample component (i.e., a metabolite, molecule, or ion) in each of the plurality of samples, from the two-dimensional data set representing that selected sample component. In doing so, the sample component to be analyzed is first determined by selecting an intensity peak (see, e.g., element 225 in FIG. 3) generally present with sufficient quality in each of the plurality of two-dimensional data sets of metabolomics data (see, e.g., element 225 in FIG. 5, step 700 in FIG. 7). As previously disclosed, such two-dimensional data sets are determined from respective three-dimensional data set of metabolomics data for each of a plurality of samples (e.g., step 700 in FIG. 7), generally by selecting or otherwise designating a particular value (i.e., retention time or sample component mass) with respect to one of the dimensions/axes of the three dimensional data set. One skilled in the art will appreciate, however, that the sample component to be analyzed may, in some instances, be selected from the three-dimensional data set, if necessary or desired, and that such selection of the sample component to be analyzed may be further refined upon analysis of the two-dimensional data set corresponding thereto. In some instances, the selection of the sample component to be analyzed may be facilitated, for example, by analyzing a graphical representation of the three-dimensional data set(s) (i.e., via user interface 150), and the selection may involve, for instance, evaluating the apparent intensity response of that sample component in the respective two-dimensional and/or three-dimensional data sets, to determine the selected intensity peak 225.

In some instances, the processor device 130 may be configured to execute computer-readable program code portions stored by the memory device 140 for analyzing the two-dimensional and/or three-dimensional data sets across two or more of the plurality of samples so as to determine a suitable sample component to be further analyzed, whether that sample component has been previously identified (i.e., as a particular molecule, ion, or metabolite) or not, via an intensity peak 225 (otherwise referred to herein as "selected intensity peak," "ion peak,", or "selected ion peak") associated therewith. That is, in order to select a suitable sample component for analysis, the processor device 130 may be configured to sort and/or group intensity/ion peak data across the plurality of samples, for example, by sample component mass and/or by selected time. In this manner, the processor device 130 may also be configured, for instance, to examine intensity peak data that is sufficiently discernible from background noise or other undesirable data artifacts (i.e., suitable quality), in order to reduce variances and provide a more statistically significant analysis upon determining the selected intensity peak 225. In one aspect, in order to determine the selected intensity peak, the processor device 130 may be configured to first identify a plurality of candidate intensity peaks in each of the two-dimensional data sets, and compare the candidate intensity peaks across the plurality of two-dimensional data sets, wherein the candidate intensity peak with the lowest standard deviation (i.e., best data quality across the plurality of samples) is selected as the selected intensity/ion peak 225. However, one skilled in the art will appreciate that the selected intensity peak may be determined in other manners. For example, upon comparing the candidate intensity peaks across the plurality of two-dimensional data sets, one of the candidate intensity peaks evident across the plurality of two-dimensional data sets, and corresponding to a recognized compound in a compound database, may be selected as the selected ion peak. More particularly, for instance, the candidate intensity peaks across the plurality of two-dimensional data sets may be compared with mass spectra included in a library or database of recognized or otherwise known compounds (i.e., in a library or database matching process), followed with subjective curation or resolution of the matching process, if necessary. In such an instance, one of the candidate intensity peaks matched with, corresponding to, or best correlated with, the recognized or known compound (i.e., by comparison of quantitative mass) may be selected as the selected intensity/ion peak 225 as shown, for example, in FIG. 6 and FIG. 8, and may facilitate or otherwise promote consistent integration or re-integration across the plurality of samples.

As part of the sorting/grouping procedure, the processor device 130 may be further configured to align the selected intensity peak 225 evident in each two-dimensional data set, across the plurality of samples, prior to further analysis of the data as shown, for example, in FIG. 5. More particularly, when analyzing spectrometry data across a plurality of samples, various compounds (including metabolites) may move at somewhat different rates during a separation process, from one sample to another, so that it may not be entirely clear which peaks (corresponding to eluted compounds, for example) should be considered as corresponding to one another across the plurality of samples. As such, the processor device 130 may be configured to execute instructions/computer readable program code portions to implement an intensity peak alignment correction method for the selected intensity peak in each two-dimensional data set across the plurality of samples. For example, one such method involves spiking known compounds into each sample that are characterized by known retention times (RT) in spectrometry analysis. The set of "spiked" compounds matches a fixed retention index (RI) value to the shifting RT. The "spiked" compounds thus provide an internal standard (IS) that may be used to align data from a plurality of samples from study to study and/or from study to a chemical library. One skilled in the art will appreciate, however, that many different methods may be used to perform the intensity peak alignment for the selected intensity peak, across the plurality of samples, within the spirit and scope of the present disclosure, and that the example presented herein in this respect is not intended to be limiting in any manner.

Once the sample component to be analyzed has been selected, and sorted/grouped and aligned via the corresponding selected intensity peak across the plurality of samples, the processor device 130 may be configured to execute instructions/computer readable program code portions to implement a procedure for determining an area associated with the selected intensity peak, using one of a plurality of integration procedures, for each of the two-dimensional data sets across the plurality of samples (see, e.g., FIG. 5, FIGS. 6a-6c, and step 710 of FIG. 7). In such instances, the area of the selected intensity peak 225 may represent, for example, a relative quantity of the corresponding sample component (i.e., molecule, ion, or metabolite) within the sample, since each two-dimensional data set is configured to indicate a sample property (i.e., sample component (retention) time) in one dimension versus a detected intensity at a selected value of another sample property (i.e., sample component mass) as a function of time in the other dimension. In such instances, the intensity may represent, for example, an amount of the molecules, ions, or metabolites having the selected value of the sample component mass, detected as a function of (retention) time, beginning from a time zero point. In determining the area associated with the selected intensity peak in each two-dimensional data set, the boundaries of that intensity peak must first be determined. In doing so, the processor device 130 may be configured to execute instructions/computer readable program code portions to determine an intensity peak origin 500 and an intensity peak terminus 550 along the sample property dimension (i.e., the sample component time axis 230) of the two-dimensional data set. In this regard, each of the intensity peak origin 500 and the intensity peak terminus 550 may not necessarily be clearly defined. That is, other sample components, background noise, or other undesirable data artifacts may sometimes impinge on or interfere with the selected intensity peak 225 in a data set, in the form of a "shoulder" or other transition about either the apparent intensity peak origin 500 or the apparent intensity peak terminus 550. As such, the determination of the intensity peak origin 500 and/or the intensity peak terminus 550 may also involve some approximations or subjective analysis such as, for example, determining a particular change in slope or other threshold change, wherein some variations may be permissible within certain tolerances without significantly affecting data quality (i.e., from a statistical perspective).

Once the intensity peak origin 500 and the intensity peak terminus 550 have been determined for the selected intensity peak 225 in each two-dimensional data set, the relation of each of the intensity peak origin 500 and the intensity peak terminus 550, with respect to a baseline intensity 575 in the intensity dimension 220, must also be determined. That is, the lower boundary of the selected intensity peak 225 must be determined for the purposes of determining the area associated therewith, across the two-dimensional data sets for the plurality of samples. Accordingly, the processor device 130 may also be configured to execute instructions/computer readable program code portions to determine an appropriate baseline intensity 575 for the selected intensity peak 225 across the two-dimensional data sets for the plurality of samples. Such a baseline intensity 575 should, in some instances, define or otherwise characterize the relative intensity origin of the selected intensity peak 225 above any background noise associated with the collected data. Upon determination of the appropriate baseline intensity 575, the processor device 130 may then be configured to execute instructions/computer readable program code portions to determine a relation of each of the intensity peak origin 500 and the intensity peak terminus 550 with respect to the baseline intensity 575 in the intensity dimension 220. In doing so, the processor device 130 is configured to determine whether each of the intensity peak origin 500 and the intensity peak terminus 550 corresponds to the baseline intensity 575 in the intensity dimension 220 (i.e., whether the intensity peak origin 500 or the intensity peak terminus 550 in the sample component mass dimension 210 has an apparent intensity corresponding to the determined baseline intensity 575 in the intensity dimension 220). If so, the intensity peak origin 500 and/or the intensity peak terminus 550 may be designated as a "base" correlation with the baseline intensity 575.

The processor device 130 may be further configured to determine whether each of the intensity peak origin 500 and the intensity peak terminus 550 is spaced apart from the baseline intensity 575 in the intensity dimension 220 (i.e., whether the intensity peak origin 500 or the intensity peak terminus 500 in the sample component time dimension 230 has an apparent intensity that is either greater than or less than the determined baseline intensity 575 in the intensity dimension 220). If so, the intensity peak origin 500 and/or the intensity peak terminus 550 may be designated as a "drop" correlation with respect to the baseline intensity 575. In such instances of a "drop" correlation, the processor device 130 may be further configured to execute instructions/computer readable program code portions to extend a "drop" boundary (see, e.g., element 600 in FIG. 5 and FIG. 6b, element 610 in FIG. 6c) from the "drop" correlated intensity peak origin and/or the "drop" correlated intensity peak terminus to the baseline intensity. In doing so, the apparent relative area for the selected intensity peak 225 in each two-dimensional data set across the plurality of samples is thus defined. In some instances, the defined area of the selected intensity peak 225 may be designated according to the nature of the intensity peak origin 500 and the intensity peak terminus 550, namely according to correlation represented by each. That is, each selected intensity peak may be designated as a "base-base" correlation (see, e.g., FIG. 6a), a "base-drop" correlation (see, e.g., FIG. 6c), a "drop-base" correlation (see, e.g., FIG. 6b), or a "drop-drop" correlation. Once the area of the selected intensity peak 225 is defined, the processor device 130 may also be configured to execute instructions/computer readable program code portions to quantify the area by integrating the selected intensity peak 225 between the intensity peak origin 500 and the intensity peak terminus 550 in the sample property dimension, with respect to the relations thereof to the baseline intensity 575 in the intensity dimension, including any boundaries represented by a "drop" boundary 600 or 610. Accordingly, the determined area associated with the selected intensity peak 225 is representative of and corresponds to a relative quantity of the sample component in the respective sample, for example, in terms of a percent relative standard deviation (% RSD).

During analysis of the selected intensity peak 225 in each of the two-dimensional data sets across the plurality of samples in a manner disclosed herein, the processor device 130 may further be configured to execute instructions/computer readable program code portions so as to identify a particular compound (i.e., a metabolite) or sample component associated with the selected and analyzed intensity peak 225 (see, e.g., step 720 in FIG. 7). The particular compound/sample component may be "known named" and/or "known, but unnamed" chemicals/compounds. That is, for example, the identified particular compound/sample component may correspond to a metabolite having a chemical nomenclature or to a "known, but unnamed" metabolite which has been previously identified, but not yet assigned a chemical name and/or classification. One skilled in the art will appreciate that such compound identification procedures may be accomplished in many different manners with respect to the selected intensity peak 225 and/or the corresponding two-dimensional or three-dimensional data set, in some instances, across the plurality of samples under analysis. For example, some compound identification procedures are disclosed in U.S. Pat. No. 7,433,787 (System, Method, and Computer Program Product Using a Database in a Computing System to Compile and Compare Metabolomic Data Obtained From a Plurality of Samples) and U.S. Pat. No. 7,561,975 (System, Method, and Computer Program Product for Analyzing Spectrometry Data to Identify and Quantify Individual Components in a Sample), as well as U.S. Patent Application Publication No. US 2009/0093971 A1 (System and Method for Analyzing Metabolomic Data), all assigned to Metabolon, Inc., which is also the assignee of the present application. To the extent that such compound identification procedures are relevant to the disclosure herein, such compound identification procedures disclosed by U.S. Pat. Nos. 7,433,787 and 7,561,975; and U.S. Patent Application Publication No. US 2009/0093971 A1 are incorporated herein by reference, and not otherwise discussed in detail herein for the sake of brevity.

In accomplishing the determination of the area associated with the selected intensity peak 225 (corresponding to an identified sample component) of each two-dimensional data set across the plurality of samples, as previously disclosed, each quantified area may then be characterized by the particular integration procedure implemented by the processor device 130 for determining that area. That is, the particular integration procedure implemented to determine the area of the selected intensity peaks may also be designated, in some instances, according to the relation of each of the intensity peak origin 500 and the intensity peak terminus 550 to the baseline intensity 575. Namely, the various integration procedures may be designated as a "base-base" integration (see, e.g., FIG. 6*a*), a "base-drop" integration (see, e.g., FIG. 6*c*), a "drop-base" integration (see, e.g., FIG. 6*b*), or a "drop-drop" integration. One skilled in the art will appreciate, however, that the area of the selected intensity peak 225 determined by the various integration procedures may vary according to the particular integration procedure used by the processor device 130. That is, an intensity peak area determined by a "drop-drop" integration procedure may, in some instances, be significantly different (i.e., in a statistical manner) from an intensity peak area determined by a "base-base" integration procedure, since the latter may also include a contribution of a "tail" portion of the peak about both the intensity peak origin 500 and the intensity peak terminus 550. Since the area of the selected intensity peak 225 for each two-dimensional data set, across the plurality of samples, may sometimes be used in a cumulative (or at least semi-cumulative) manner in subsequent processes (i.e., determining an "average" relative quantity of the sample component corresponding to the selected intensity peak 225 across the plurality of samples), such variation in the particular integration procedure may, in some instances, become statistically significant with respect to the determined relative quantity of the particular sample component, represented by the selected intensity peak 225, when analyzed across the plurality of samples.

According to further aspects of the present application, the processor device 130 may thus be further configured to execute instructions/computer readable program code portions so as to determine the one of the plurality of integration procedures used to determine the area associated with the selected intensity peak 225 for each of the two-dimensional data sets across the plurality of samples, in terms of a combination of the determined relation of the intensity peak origin 500 to the baseline intensity 575 and the determined relation of the intensity peak terminus 550 to the baseline intensity 575. That is, the processor device 130 may also be configured to determine whether the applied integration procedure for originally determining the area of each intensity peak was a "base-base" integration, a "base-drop" integration, a "drop-base" integration, or a "drop-drop" integration. The determined areas of the selected intensity peak may then be compared across the two-dimensional data sets and grouped, according to the particular integration procedure originally implemented by the processor device 130. In doing so, the processor device 130 may also be configured to determine the particular integration procedure used to calculate the area of the selected intensity peak 225 for a first portion of the two-dimensional data sets (see, e.g., step 730 in FIG. 7). In some instances, the first portion may represent a majority of the two-dimensional data sets across the plurality of samples. However, where more than two different integration procedures have been used, the first portion may represent the particular integration procedure implemented in more instances than any of the other integration procedures. In any instance, the particular one of the integration procedures determined by the processor device 130 may be designated as a template integration procedure for the selected intensity peaks in the two-dimensional data sets across the plurality of samples. That is, the processor device 130 may also be configured to execute instructions/computer readable program code portions to determine and designate the template integration procedure and to apply the template integration procedure to the selected intensity peaks of a second portion of the two-dimensional data sets, wherein the second portion of the two-dimensional data sets previously had the areas of the selected intensity peaks thereof determined by one of the integration procedures other than the template integration procedure (see, e.g., step 740 in FIG. 7). Effectively, the processor device 130 may be configured to re-calculate the area of the selected intensity peak 225 for each two-dimensional data set, where the area of the selected intensity peak 225 was originally determined by an integration procedure other than the template (i.e., most prevalently applied) integration procedure.

One skilled in the art will appreciate, however, that the template integration procedure may not necessarily be applicable to re-calculate the selected intensity peak area for some of the two-dimensional data sets. For example, an attempt to apply the template integration procedure to a selected intensity peak 225, having an initially-determined area not previously determined by that integration procedure, may not be possible in some cases due, for instance, to background noise or other undesirable data artifacts that render uncertain the intensity peak origin 500 or the intensity peak terminus 550 of the selected intensity peak 225 in that particular two-dimensional data set. Accordingly, in some instances, the application of the template integration procedure to re-calculate the areas of certain selected intensity peaks may be subject to an applicability procedure implemented by the processor device 130. If such instances do arise, however, the corresponding inapplicability of the template integration procedure may be statistically addressed in any subsequent cumulative, or at least partially cumulative, analysis across the plurality of samples. In any instance, the re-calculation of the areas of the selected intensity peaks not previously determined by the template integration procedure may serve, for example, to adjust the relative quantity of the particular sample component determined to be in the samples, by way of the areas of the corresponding selected intensity peaks of the second portion of the two-dimensional data sets, with respect to the relative quantity of the sample component determined to be in the samples corresponding to the first portion of the two-dimensional data sets. In this manner, the processor device 130 may be configured to apply a more consistent determination of the area of the selected intensity peak for each of the two-dimensional data sets across the plurality of samples, so as to achieve increased quality and consistency of the analysis results (i.e., the relative quantity of the sample component across the plurality of samples) that may be significant, statistically or otherwise, in subsequent analyses of the data.

In other aspects, the processor device 130 may also be configured to cooperate with the memory device 140 to execute instructions/computer readable program code portions for further analyzing the selected intensity peak and/or the corresponding two-dimensional and three-dimensional data sets across the plurality of samples so as to determine a trend or other relationship across the plurality of samples. For example, the profile shown in FIG. 3, in the case of some samples 100, may correlate to a known metabolite and/or a known, but unnamed metabolite, with sufficient certainty (which may be shown as a data point within a selected time frame 260, 270, as shown in FIG. 4, wherein the data point may represent, for example, the selected intensity peak in the corresponding two-dimensional data set). However, due to variations in samples, potential contaminants within samples 100, and/or other experimental factors that will be appreciated by those skilled in the art, some three-dimensional data sets generated by the analysis of some samples 100 may result in corresponding two-dimensional time versus response intensity profiles for a given sample component mass that may not match an identified compound with such sufficient certainty, or which may not be aligned with respect to the selected intensity peak across the plurality of samples. Aspects of the present disclosure may thus further comprise a user interface 150 in communication with said processor device 130/memory device 140 for displaying a visual indication 160 (see also, FIG. 4, for example) comparisons across the plurality of samples 100 on a time axis 240 that is indicative of the time 265 at which selected intensity peaks for the given sample component mass were determined from the data detected by the analytical device 110. The user interface 150 may be capable of displaying to the user, for example, a display 160 of sample number 250 (indicating the identity of the sample 100) versus time 240, as shown generally in FIG. 4. More particularly, in some aspects, the user interface 150, in communication with the database/processor device 130, may be configured to display a visual indication 160 of a comparison of the selected intensity peak 225 data for each of the two-dimensional data sets, across the plurality of samples for facilitating analysis (i.e., to facilitate intensity peak alignment) across the samples in a succinct graphical format that spans a "fourth dimension" across the population of samples. The user interface 150 may comprise, for example, a display device, personal computer, and/or other electronic device having a display for graphical representation of data.

According to another aspect of the present disclosure, there may be instances in which the selected intensity peaks may indicate or otherwise be comprised of more than one sample component. In such instances, accuracy in the quantization of the particular sample component of interest, as well as the second component or other identified components, may be realized as further disclosed herein. More particularly, as previously disclosed, once the selected intensity peaks to be analyzed have been identified (see, e.g., step 900 in FIG. 9), sorted/grouped and aligned across the plurality of samples, the processor device 130 may be configured to execute instructions/computer readable program code portions to implement a procedure for determining an area associated with each of the selected intensity peaks, using one of a plurality of integration procedures, for each of the corresponding two-dimensional data sets across the plurality of samples (see, e.g., step 910 in FIG. 9). Accordingly, the area of each of the selected intensity peaks across the plurality of samples is determined on the premise that the selected intensity peak represents a single sample component. In such instances, the area of the selected intensity peak 225 may represent, for example, a relative quantity of the single sample component within the sample, since each two-dimensional data set is configured to indicate a detected intensity of the selected sample component mass in one dimension versus a sample component time in the other dimension (thus intensity of the selected sample component mass is indicated as a function of time). That is, as previously discussed, the intensity may represent, for example, an amount of the molecules, ions, or metabolites having the selected value of the sample component mass, detected as a function of (retention) time, beginning from a time zero point.

In determining the area associated with the selected intensity peak in each two-dimensional data set, the boundaries of that intensity peak must first be determined. In doing so, the processor device 130 may be configured to execute instructions/computer readable program code portions to determine an intensity peak origin 500 and an intensity peak terminus 550 along the sample property dimension (i.e., the sample component time axis 230) of the two-dimensional data set. In this regard, each of the intensity peak origin 500 and the intensity peak terminus 550 may not necessarily be clearly defined. That is, other sample components, background noise, or other undesirable data artifacts may sometimes impinge on or interfere with the selected intensity peak 225 in a data set, in the form of a "shoulder," "secondary peak," or other transition about either the apparent intensity peak origin 500 or the apparent intensity peak terminus 550. As such, the determination of the intensity peak origin 500 and/or the intensity peak terminus 550 may also involve some approximations or subjective analysis such as, for example, determining a particular change in slope or other threshold change, wherein some variations may be permissible within certain tolerances without significantly affecting data quality (i.e., from a statistical perspective).

Once the intensity peak origin 500 and the intensity peak terminus 550 have been determined for the selected intensity peak 225 in each two-dimensional data set, the relation of each of the intensity peak origin 500 and the intensity peak terminus 550, with respect to a baseline intensity 575 in the intensity dimension 220, must also be determined. That is, the lower boundary of the selected intensity peak 225 must be determined for the purposes of determining the area associated therewith, across the two-dimensional data sets for the plurality of samples. Accordingly, the processor device 130 may also be configured to execute instructions/computer readable program code portions to determine an appropriate baseline intensity 575 for the selected intensity peak 225 across the two-dimensional data sets for the plurality of samples. Such a baseline intensity 575 should, in some instances, define or otherwise characterize the relative intensity origin of the selected intensity peak 225 above any background noise associated with the collected data. Upon determination of the appropriate baseline intensity 575, the processor device 130 may then be configured to execute instructions/computer readable program code portions to determine a relation of each of the intensity peak origin 500 and the intensity peak terminus 550 with respect to the baseline intensity 575 in the intensity dimension 220. In doing so, the apparent relative area for the selected intensity peak 225 in each two-dimensional data set across the plurality of samples is defined. In some instances, the defined area of the selected intensity peak 225 may be designated according to the nature of the intensity peak origin 500 and the intensity peak terminus 550, namely according to correlation represented by each. That is, each selected intensity peak may be designated as a "base-base" correlation, a "base-drop" correlation, a "drop-base" correlation, or a "drop-drop" correlation. Once the boundary of the selected intensity peak 225 is defined, the processor device 130 may also be configured to execute instructions/computer readable program code portions to quantify the area by integrating the selected intensity peak 225 between the intensity peak origin 500 and the intensity peak terminus 550 in the sample property dimension, with respect to the relations thereof to the baseline intensity 575 in the intensity dimension, including any boundaries represented by a "drop" boundary 600 or 610. Accordingly, the determined area associated with the selected intensity peak 225 is representative of and corresponds to a relative quantity of the sample component in the respective sample, for example, in terms of a percent relative standard deviation (% RSD).

During analysis of the selected intensity peak 225 in each of the two-dimensional data sets across the plurality of samples in a manner disclosed herein, the processor device 130 may further be configured to execute instructions/computer readable program code portions so as to identify a particular compound (i.e., a metabolite) or sample component associated with the selected and analyzed intensity peak 225 (see, e.g., step 920 in FIG. 9). The particular compound/sample component may be "known named" and/or "known, but unnamed" chemicals/compounds. That is, for example, the identified particular compound/sample component may correspond to a metabolite having a chemical nomenclature or to a "known, but unnamed" metabolite which has been previously identified, but not yet assigned a chemical name and/or classification. One skilled in the art will appreciate that such compound identification procedures may be accomplished in many different manners with respect to the selected intensity peak 225 and/or the corresponding two-dimensional or three-dimensional data set, in some instances, across the plurality of samples under analysis. One skilled in the art will thus appreciate that, thus far, the further disclosed aspect is similar to previously disclosed aspects, for example, in determining the boundary of a selected intensity peak, integrating the area of the selected intensity peak to determine the relative quantity of the sample component represented thereby, and identifying the particular compound/sample component (for example, from a library match).

As previously discussed, according to some aspects of the present application, in order to verify and/or adjust the initial analysis, the processor device 130 may be configured to execute instructions/computer readable program code portions so as to determine whether a predetermined one of the plurality of integration procedures was used to determine the area associated with the selected intensity peak 225 for any of the two-dimensional data sets across the plurality of samples, in terms of a combination of the determined relation of the intensity peak origin 500 to the baseline intensity 575 and the determined relation of the intensity peak terminus 550 to the baseline intensity 575. That is, the processor device 130 may also be configured to determine whether the applied integration procedure for originally determining the area of each intensity peak was a "base-base" integration, a "base-drop" integration, a "drop-base" integration, or a "drop-drop" integration.

In one aspect, an applied integration procedure comprising a "base-base" integration may be characterized as indicating an independent selected intensity peak. In other aspects, a "drop-drop" integration may be characterized as indicating that the selected intensity peak is a "middle" peak. That is, in those aspects, the "base-base" and "drop-drop" integrations may indicate that the selected intensity peak stands isolated amid the background and other sample components. However, in yet another aspect, a "base-drop" integration or a "drop-base" integration may be characterized as indicating the presence of a "shoulder" or secondary peak, wherein the "base-drop" integration may indicate that the shoulder is disposed about or otherwise in proximity to the trailing edge of the selected intensity peak, and the "drop-base" integration may indicate that the shoulder is disposed about or otherwise in proximity to the leading edge of the peak.

Accordingly, in order to determine whether the initial analysis may be improved, it may be helpful to determine whether the initial analysis was sufficiently premised on the selected intensity peak being representative of a single sample component. In doing so, the predetermined one of the plurality of integration procedures is selected as one (or both) of the "base-drop" and "drop-base" integrations. The determined areas of the selected intensity peak may then be compared across the two-dimensional data sets and grouped, according to the particular integration procedure originally implemented by the processor device 130. If such "base-drop" and/or "drop-base" integrations are present in the initial analysis, the inference of a shoulder or secondary peak may be further indicative of the presence of a second sample component in the analyzed sample (see, e.g., step 930 in FIG. 9). One skilled in the art will appreciate, however, that the particular "base-drop" and/or "drop-base" integrations may not be consistently identifiable across the two-dimensional data sets. More particularly, for example, one of the intensity peak origin and the intensity peak terminus may be consistently at or about the baseline, while the other of the intensity peak origin and the intensity peak terminus may be mixed as either a "base" or a "drop." In other instances, both the intensity peak origin and the intensity peak terminus may indicate mixed or otherwise varied results with respect to being a "base" or a "drop." In such instances, a subjective evaluation may be made as to whether a second sample component may be present with respect to the selected intensity peak across the two-dimensional data sets (i.e., by "flagging" certain peaks for subjective/manual inspection and subjective/manual integration, a list of "suspect" peaks for subjective or human evaluation is created), and the verification disclosed herein may be continued, or the verification disclosed herein may be terminated as unnecessary.

As shown in FIG. 8, the processor device 130 may be configured to determine the particular integration procedure used to calculate the area of the selected intensity peak 225 and, in instances of the processor device 130 determining that the predetermined one of the integration procedures was used in the initial analysis, the processor device 130 may further be configured to execute instructions/computer readable program code portions so as to designate the two-dimensional data sets implementing that integration procedure as a first portion of the selected intensity peaks of the two-dimensional data sets. In doing so, the determined areas of the selected intensity peaks, according to the predetermined (base-drop and/or drop-base) one of the integration procedures, may be designated as representing the presence and quantity of a first sample component. That is, the determined areas of the selected intensity peak for the two-dimensional data sets of the first portion may be designated as indicating a first sample component, while the excluded portion of the area of the respective selected intensity peak may indicate the presence of a second sample component (for example, as the leading edge or trailing edge shoulder to the selected intensity peak (or "primary" peak)—see, e.g., samples 2, 3, and 8 of FIG. 8). From another perspective, the selected intensity peaks may be compared across the plurality of two-dimensional data sets to determine whether any of the areas thereof associated with the first sample component were determined by the predetermined one of the integration procedures, indicative of a shoulder peak in addition to a primary peak, corresponding to the second sample component in addition to the first sample component, wherein the selected intensity peaks having the areas thereof associated with the first sample component determined by the predetermined one of the integration procedures will thus comprise the first portion of the selected intensity peaks of the two-dimensional data sets. Thus, the first portion of the selected intensity peaks of the two-dimensional data sets may indicate a second sample component associated therewith in addition to the first sample component. In such instances, the predetermined one of the integration procedures used to determine the area of each selected intensity peak of the first portion associated with the first sample component may thus comprise a first sample component mask integration procedure. further, an area of each selected intensity peak, corresponding to a relative quantity of the second sample component (i.e., the leading edge or trailing edge shoulder to the selected intensity peak), may also be determined for the first portion of the selected intensity peaks of the two-dimensional data sets, using a second sample component mask integration procedure (see, e.g., step 940 in FIG. 9). That is, one skilled in the art will appreciate that the previously disregarded area under the selected intensity peak corresponding to the second sample component may also be integrated according to an appropriate integration procedure so as to provide an indication of the relative quantity of the second sample component in the respective sample.

If the predetermined one of integration procedures was not used to determine the area associated with the first sample component of a first portion of the selected intensity peaks, the verification and adjustment procedure may revert to one of the aspects previously disclosed, for example, using the "majority" integration procedure or the particular integration procedure implemented in more instances than any of the other integration procedures as a template integration procedure, and then applying the template integration procedure to the selected intensity peaks of a remainder portion of the two-dimensional data sets previously having the areas of the selected intensity peaks thereof determined by one of the integration procedures other than the template integration procedure, to adjust the relative quantity of the sample component determined to be in the samples corresponding to the remainder portion of the two-dimensional data sets with respect to the relative quantity of the sample component determined to be in the samples corresponding to the identified portion of the two-dimensional data sets.

However, if the predetermined one of integration procedures was used to determine the area associated with the first sample component of a first portion of the selected intensity peaks, once the first portion of the selected intensity peaks of the two-dimensional data sets is determined, the processor device 130 may further be configured to execute instructions/ computer readable program code portions so as to apply the first and second sample component mask integration procedures to the selected intensity peaks of a second portion of the two-dimensional data sets (see, e.g., step 950 in FIG. 9). The second portion may be, for example, the remainder or any remaining portion of the two-dimensional data sets previously having the areas of the selected intensity peaks thereof determined by one of the integration procedures other than the first sample component mask integration procedure (see, e.g., samples 1, 4-7, and 9 of FIG. 8, the initially-calculated areas of the selected intensity peaks being indicated by the dashed lines extending between the intensity peak origin and the intensity peak terminus). As such, in applying the first and second sample component mask integration procedures to the selected intensity peaks of the second portion of the two-dimensional data sets (i.e., those two-dimensional data sets previously analyzed using a base-base or drop-drop integration procedure), the respective areas thereof, previously attributed to a single sample component in the initial analysis, may be adjusted to indicate the relative quantities of the first and second sample components determined to be present in the samples corresponding to the second portion of the two-dimensional data sets with respect to the relative quantities of the first and second sample components determined to be present in the samples corresponding to the first portion of the two-dimensional data sets.

From another perspective, upon determining the first portion of the selected intensity peaks of the two-dimensional data sets, a primary peak, a shoulder peak, and a peak transition therebetween may be determined for each of the selected intensity peaks comprising the first portion of the selected intensity peaks of the two-dimensional data sets indicating the second sample component in addition to the first sample component. As one aspect of the verification procedure, the identity of the second sample component associated with the shoulder peaks of the first portion of the selected intensity peaks of the two-dimensional data sets may be determined, for example, by comparison to a library of known components. In some instances, since the initial analysis of the two-dimensional data sets may include some variation in the parameters used to determine the integrated areas of the selected intensity peaks, the first and second sample component mask integration procedures may each represent an average, median, or other representation of the integration parameters across the first portion, wherein the first sample component mask integration procedure may also be compared to the second sample component mask integration procedure so as to determine a representative peak transition in the sample property dimension between the primary peak and the shoulder peak, and a representative baseline intensity in the intensity dimension. Further, in applying the first and second sample component mask integration procedures to the selected intensity peaks of a second portion of the two-dimensional data sets, the first sample component mask integration procedure may be executed with respect to the second portion of selected intensity peaks, using the intensity peak origin and the representative peak transition in the sample property dimension with respect to the representative baseline intensity in the intensity dimension, to determine the area of the selected intensity peaks of the second portion associated with the first sample component. Similarly, the second sample component mask integration procedure may be executed with respect to the second portion of selected intensity peaks, using the representative peak transition and the intensity peak terminus in the sample property dimension with respect to the representative baseline intensity in the intensity dimension, to determine the area of the selected intensity peaks of the second portion associated with the first sample component.

One skilled in the art will appreciate, as shown in FIG. 8, that the "re-integration" or verification procedure according to such aspects of the present disclosure may provide significantly (statistically or otherwise) different results with respect to the quantity of the first sample component present in the analyzed samples, with respect to the original integration, as well as with respect to the second sample component. In some instances, a further level of verification may be provided, and implemented as necessary or desired. For example, aspects of the present disclosure may provide that any or all of the selected data peaks of the two-dimensional data sets may be automatically determined and/or manually conducted. More particularly, for instance, with respect to the peak transition between the primary peak and the shoulder peak, if present, the processor device 130 may further be configured to execute instructions/computer readable program code portions so as to allow an automatically-determined peak transition in any or all of the two-dimensional data sets to be manually moved or otherwise adjusted based upon a subjective evaluation of the results of the automatic procedure, wherein such manual manipulation may allow, for example, a subject matter expert to further refine the analysis results. Such aspects of the present disclosure thus address and reduce quantitative inaccuracies at early stages of a metabolomics analysis, and may thus advantageously facilitate avoidance, reduction, or minimization of larger inaccuracies in subsequent steps or analyses.

Aspects of the present disclosure also provide methods of analyzing metabolomics data, as shown generally in the operational flow diagrams of FIGS. 7 and 9, and as previously discussed herein. In addition to providing appropriate apparatuses and methods, aspects of the present disclosure may also provide associated computer program products for performing the functions/operations/steps disclosed above, in the form of, for example, a computer-readable storage medium (i.e., memory device 140) having particular computer-readable program code portions stored therein by the medium that, in response to execution by the processor device 130, cause the apparatus to at least perform the steps disclosed herein. In this regard, FIGS. 7 and 9 are an operational flow diagram associated with particular methods, apparatuses and computer program products according to aspects of the present disclosure. It will be understood that each block or step of the operational flow diagram or combinations of blocks in the operational flow diagram can be implemented by appropriate computer program instructions executed by the processor device 130. These computer program instructions may be loaded onto a computer device or other programmable apparatus for executing the functions specified in the operational flow diagram otherwise associated with the method(s) disclosed herein. These computer program instructions may also be stored in a computer-readable memory (i.e., memory device 140), so as to be accessible by a computer device or other programmable apparatus in a particular manner, such that the executable instructions stored in the computer-readable memory may produce or facilitate the operation of an article of manufacture capable of directing or otherwise executing the instructions which implement the functions specified in the operational flow diagram otherwise associated with the method(s) disclosed herein. The computer program instructions may also be loaded onto a computer device or other programmable apparatus to cause a series of operational steps to be performed on the computer device or other programmable apparatus to produce a computer-implemented process such that the instructions executed by the computer device or other programmable apparatus provide or otherwise direct appropriate steps for implementing the functions/steps specified in the operational flow diagram otherwise associated with the method(s) disclosed herein. It will also be understood that each step of the operational flow diagram, or combinations of steps in the operational flow diagram, can be implemented by special purpose hardware-based computer systems which perform the specified functions or steps, or combinations of special purpose hardware and computer instructions (software).

Many modifications and other aspects of the disclosure set forth herein will come to mind to one skilled in the art to which this disclosure pertain having the benefit of the teachings presented in the foregoing descriptions and the associated drawings. Therefore, it is to be understood that the disclosure is not to be limited to the specific aspects disclosed and that modifications and other aspects are intended to be included within the scope of the appended claims. Although specific terms are employed herein, they are used in a generic and descriptive sense only and not for purposes of limitation.

That which is claimed:

1. A method of analyzing data obtained from a component separation and mass spectrometer system, comprising:
    determining a selected ion peak in each of a plurality of two-dimensional data sets including data obtained from the component separation and mass spectrometer system, each of the two-dimensional data sets being determined from a respective three-dimensional data set, including the data obtained from the component separation and mass spectrometer system, for each of a plurality of samples;
    determining an area associated with the selected ion peak, using one of a plurality of integration procedures, for each of the two-dimensional data sets;
    determining an identity of a sample component associated with the selected ion peaks of the two-dimensional data sets, the area associated with each selected ion peak further corresponding to a relative quantity of the sample component in the respective sample;
    comparing the selected ion peaks across the plurality of two-dimensional data sets to determine the one of the integration procedures used to determine the area of the selected ion peak for a first portion of the two-dimensional data sets, the determined one of the integration procedures comprising a template integration procedure; and
    applying the template integration procedure to the selected ion peaks of a second portion of the two-dimensional data sets, the second portion of the two-dimensional data sets previously having the areas of the selected ion peaks thereof determined by one of the integration procedures other than the template integration procedure, to adjust the relative quantity of the sample component determined to be in the samples corresponding to the second portion of the two-dimensional data sets with respect to the relative quantity of the sample component determined to be in the samples corresponding to the first portion of the two-dimensional data sets.

2. A method according to claim 1, wherein the two-dimensional data sets are configured to indicate a sample property in one dimension versus an intensity of a selected value of another sample property in the other dimension, and determining an area associated with the selected ion peak, further comprises:
    determining an intensity peak origin and an intensity peak terminus in the sample property dimension;
    determining a relation of each of the intensity peak origin and the intensity peak terminus with respect to a baseline intensity in the intensity dimension; and
    integrating the selected ion peak between the intensity peak origin and the intensity peak terminus in the sample property dimension, with respect to the relations thereof to the baseline intensity in the intensity dimension, so as to determine the area associated with the selected ion peak.

3. A method according to claim 2, wherein determining an intensity peak origin and an intensity peak terminus in the sample property dimension further comprises determining an intensity peak origin and an intensity peak terminus in a time dimension.

4. A method according to claim 2, wherein determining a relation of each of the intensity peak origin and the intensity peak terminus with respect to a baseline intensity in the intensity dimension further comprises at least one of:
   determining whether either of the intensity peak origin and the intensity peak terminus corresponds to the baseline intensity; and
   determining whether either of the intensity peak origin and the intensity peak terminus is spaced apart from the baseline intensity.

5. A method according to claim 4, further comprising determining the one of the plurality of integration procedures used to determine the area associated with the selected ion peak for each of the two-dimensional data sets, according to a combination of the determined relation of the intensity peak origin to the baseline intensity and the determined relation of the intensity peak terminus to the baseline intensity.

6. A method according to claim 1, further comprising determining each of the two-dimensional data sets from a respective three-dimensional data set for each of a plurality of samples, each three-dimensional data set comprising a sample component mass dimension, an intensity dimension, and a time dimension.

7. A method according to claim 6, wherein determining a selected ion peak in each of a plurality of two-dimensional data sets further comprises determining a selected ion peak in each of a plurality of two-dimensional sets, with each two dimensional data set comprising the time dimension and the intensity dimension, for a selected sample component mass in the sample component mass dimension of the corresponding three-dimensional data set.

8. A method according to claim 7, further comprising comparing the selected ion peaks of the two-dimensional data sets across the plurality of two-dimensional data sets and aligning the selected ion peaks according to respective intensity characteristics across the two-dimensional data sets.

9. A method according to claim 1, wherein determining an area associated with the selected ion peak for each of the two-dimensional data sets further comprises determining an area associated with the selected ion peak for each of the two-dimensional data sets in association with a percent relative standard deviation.

10. A method according to claim 1, wherein determining a selected ion peak in each of a plurality of two-dimensional data sets further comprises:
    identifying a plurality of candidate intensity peaks in each of the two-dimensional data sets;
    comparing the candidate intensity peaks across the plurality of two-dimensional data sets; and
    selecting one of the candidate intensity peaks evident across the plurality of two-dimensional data sets, and corresponding to a recognized compound in a compound database, as the selected ion peak.

11. A method of analyzing data obtained from a component separation and mass spectrometer system, comprising:
    determining a selected ion peak in each of a plurality of two-dimensional data sets, each of the two-dimensional data sets being determined from a respective three-dimensional data set including data obtained from the component separation and mass spectrometer system, for each of a plurality of samples;
    determining an area associated with the selected ion peak, using one of a plurality of integration procedures, for each of the two-dimensional data sets;
    determining an identity of a first sample component associated with the selected ion peaks of the two-dimensional data sets, the area of each selected ion peak associated with the first sample component further corresponding to a relative quantity of the first sample component in the respective sample;
    comparing the selected ion peaks across the plurality of two-dimensional data sets to determine whether a predetermined one of the integration procedures was used to determine the area associated with the first sample component of a first portion of the selected ion peaks of the two-dimensional data sets, the first portion of the selected ion peaks of the two-dimensional data sets indicating a second sample component associated therewith in addition to the first sample component, the predetermined one of the integration procedures used to determine the area of each selected ion peak of the first portion associated with the first sample component comprising a first sample component mask integration procedure;
    determining, if the predetermined one of integration procedures was used to determine the area associated with the first sample component of the first portion of the selected ion peaks, an area of each selected ion peak, corresponding to a relative quantity of the second sample component, for the first portion of the selected ion peaks of the two-dimensional data sets, using a second sample component mask integration procedure; and
    applying the first and second sample component mask integration procedures to the selected ion peaks of a second portion of the two-dimensional data sets, the second portion of the two-dimensional data sets previously having the areas of the selected ion peaks thereof determined by one of the integration procedures other than the first sample component mask integration procedure, so as to adjust the relative quantities of the first and second sample components determined to be in the samples corresponding to the second portion of the two-dimensional data sets with respect to the relative quantities of the first and second sample components determined to be in the samples corresponding to the first portion of the two-dimensional data sets.

12. A method according to claim 11, further comprising:
    comparing, if the predetermined one of integration procedures was not used to determine the area associated with the first sample component of a first portion of the selected ion peaks, the selected ion peaks across the plurality of two-dimensional data sets to determine the one of the integration procedures used to determine the area of each selected ion peak for an identified portion of the two-dimensional data sets, the determined one of the integration procedures comprising a template integration procedure; and
    applying the template integration procedure to the selected ion peaks of a remainder portion of the two-dimensional data sets, the remainder portion of the two-dimensional data sets previously having the areas of the selected ion peaks thereof determined by one of the integration procedures other than the template integration procedure, to adjust the relative quantity of the sample component determined to be in the samples corresponding to the remainder portion of the two-dimensional data sets with respect to the relative quantity of the sample component determined to be in the samples corresponding to the identified portion of the two-dimensional data sets.

13. A method according to claim 11, wherein the two-dimensional data sets are configured to indicate a sample property in one dimension versus an intensity of a selected value of another sample property in the other dimension, and determining an area associated with the selected ion peak, further comprises:
determining an intensity peak origin and an intensity peak terminus in the sample property dimension;
determining a relation of each of the intensity peak origin and the intensity peak terminus with respect to a baseline intensity in the intensity dimension; and
integrating the selected ion peak between the intensity peak origin and the intensity peak terminus in the sample property dimension, with respect to the relations thereof to the baseline intensity in the intensity dimension, so as to determine the area associated with the selected ion peak.

14. A method according to claim 13, wherein determining an intensity peak origin and an intensity peak terminus in the sample property dimension further comprises determining an intensity peak origin and an intensity peak terminus in a time dimension.

15. A method according to claim 13, wherein determining a relation of each of the intensity peak origin and the intensity peak terminus with respect to a baseline intensity in the intensity dimension further comprises at least one of:
determining whether either of the intensity peak origin and the intensity peak terminus corresponds to the baseline intensity; and
determining whether either of the intensity peak origin and the intensity peak terminus is spaced apart from the baseline intensity.

16. A method according to claim 15, further comprising determining the one of the plurality of integration procedures used to determine the area associated with the selected ion peak for each of the two-dimensional data sets, according to a combination of the determined relation of the intensity peak origin to the baseline intensity and the determined relation of the intensity peak terminus to the baseline intensity.

17. A method according to claim 11, further comprising determining each of the two-dimensional data sets from a respective three-dimensional data set for each of a plurality of samples, each three-dimensional data set comprising a sample component mass dimension, an intensity dimension, and a time dimension.

18. A method according to claim 17, wherein determining a selected ion peak in each of a plurality of two-dimensional data sets further comprises determining a selected ion peak in each of a plurality of two-dimensional sets, with each two dimensional data set comprising the time dimension and the intensity dimension, for a selected sample component mass in the sample component mass dimension of the corresponding three-dimensional data set.

19. A method according to claim 18, further comprising comparing the selected ion peaks of the two-dimensional data sets across the plurality of two-dimensional data sets and aligning the selected ion peaks according to respective intensity characteristics across the two-dimensional data sets.

20. A method according to claim 11, wherein determining an area associated with the selected ion peak for each of the two-dimensional data sets further comprises determining an area associated with the selected ion peak for each of the two-dimensional data sets in association with a percent relative standard deviation.

21. A method according to claim 11, wherein determining a selected ion peak in each of a plurality of two-dimensional data sets further comprises:
identifying a plurality of candidate intensity peaks in each of the two-dimensional data sets;
comparing the candidate intensity peaks across the plurality of two-dimensional data sets; and
selecting one of the candidate intensity peaks evident across the plurality of two-dimensional data sets, and corresponding to a recognized compound in a compound database, as the selected ion peak.

22. A method according to claim 12, wherein comparing the selected ion peaks across the plurality of two-dimensional data sets, further comprises comparing the selected ion peaks across the plurality of two-dimensional data sets to determine whether any of the areas thereof associated with the first sample component were determined by the predetermined one of the integration procedures, indicative of a shoulder peak in addition to a primary peak, corresponding to the second sample component in addition to the first sample component, the selected ion peaks having the areas thereof associated with the first sample component determined by the predetermined one of the integration procedures comprising the first portion of the selected ion peaks of the two-dimensional data sets.

23. A method according to claim 22, further comprising determining a primary peak, a shoulder peak, and a peak transition therebetween, for each of the selected ion peaks comprising the first portion of the selected ion peaks of the two-dimensional data sets indicating the second sample component in addition to the first sample component.

24. A method according to claim 23, further comprising determining an identity of the second sample component associated with the shoulder peaks of the first portion of the selected ion peaks of the two-dimensional data sets.

25. A method according to claim 24, further comprising comparing the first sample component mask integration procedure to the second sample component mask integration procedure so as to determine a representative peak transition in the sample property dimension between the primary peak and the shoulder peak, and a representative baseline intensity in the intensity dimension.

26. A method according to claim 25, wherein applying the first and second sample component mask integration procedures to the selected ion peaks of a second portion of the two-dimensional data sets, further comprises:
executing the first sample component mask integration procedure with respect to the second portion of selected ion peaks, using the intensity peak origin and the representative peak transition in the sample property dimension with respect to the representative baseline intensity in the intensity dimension, to determine the area of the selected ion peaks of the second portion associated with the first sample component; and
executing the second sample component mask integration procedure with respect to the second portion of selected ion peaks, using the representative peak transition and the intensity peak terminus in the sample property dimension with respect to the representative baseline intensity in the intensity dimension, to determine the area of the selected ion peaks of the second portion associated with the first sample component.

27. An apparatus for analyzing data obtained from a component separation and mass spectrometer system, the apparatus comprising a processor and a memory storing executable instructions that, in response to execution by the processor, cause the apparatus to at least perform the steps of:

determining a selected ion peak in each of a plurality of two-dimensional data sets including data obtained from the component separation and mass spectrometer system, each of the two-dimensional data sets being determined from a respective three-dimensional data set, including the data obtained from the component separation and mass spectrometer system, for each of a plurality of samples;

determining an area associated with the selected ion peak, using one of a plurality of integration procedures, for each of the two-dimensional data sets;

determining a sample component associated with the selected ion peaks of the two-dimensional data sets, the area associated with each selected ion peak further corresponding to a relative quantity of the sample component in the respective sample;

comparing the selected ion peaks across the plurality of two-dimensional data sets to determine the one of the integration procedures used to determine the area of the selected ion peak for a first portion of the two-dimensional data sets, the determined one of the integration procedures comprising a template integration procedure; and applying the template integration procedure to the selected ion peaks of a second portion of the two-dimensional data sets, the second portion of the two-dimensional data sets previously having the areas of the selected ion peaks thereof determined by one of the integration procedures other than the template integration procedure, to adjust the relative quantity of the sample component determined to be in the samples corresponding to the second portion of the two-dimensional data sets with respect to the relative quantity of the sample component determined to be in the samples corresponding to the first portion of the two-dimensional data sets.

28. An apparatus according to claim 27, wherein the two-dimensional data sets are configured to indicate a sample property in one dimension versus an intensity of a selected value of another sample property in the other dimension, and determining an area associated with the selected ion peak, further comprises:

determining an intensity peak origin and an intensity peak terminus in the sample property dimension;

determining a relation of each of the intensity peak origin and the intensity peak terminus with respect to a baseline intensity in the intensity dimension; and integrating the selected ion peak between the intensity peak origin and the intensity peak terminus in the sample property dimension, with respect to the relations thereof to the baseline intensity in the intensity dimension, so as to determine the area associated with the selected ion peak.

29. An apparatus according to claim 28, wherein determining an intensity peak origin and an intensity peak terminus in the sample property dimension further comprises determining an intensity peak origin and an intensity peak terminus in a time dimension.

30. An apparatus according to claim 28, wherein determining a relation of each of the intensity peak origin and the intensity peak terminus with respect to a baseline intensity in the intensity dimension further comprises at least one of:

determining whether either of the intensity peak origin and the intensity peak terminus corresponds to the baseline intensity; and determining whether either of the intensity peak origin and the intensity peak terminus is spaced apart from the baseline intensity.

31. An apparatus according to claim 30, wherein the memory stores executable instructions that, in response to execution by the processor, cause the apparatus to further perform the step of:

determining the one of the plurality of integration procedures used to determine the area associated with the selected ion peak for each of the two-dimensional data sets, according to a combination of the determined relation of the intensity peak origin to the baseline intensity and the determined relation of the intensity peak terminus to the baseline intensity.

32. An apparatus according to claim 27, wherein the memory stores executable instructions that in response to execution by the processor cause the apparatus to further perform the step of:

determining each of the two-dimensional data sets from a respective three-dimensional data set for each of a plurality of samples, each three-dimensional data set comprising a sample component mass dimension, an intensity dimension, and a time dimension.

33. An apparatus according to claim 32, wherein determining a selected ion peak in each of a plurality of two-dimensional data sets including data obtained from a component separation and mass spectrometer system further comprises determining a selected ion peak in each of a plurality of two-dimensional sets, with each two dimensional data set comprising the time dimension and the intensity dimension, for a selected sample component mass in the sample component mass dimension of the corresponding three-dimensional data set.

34. An apparatus according to claim 32, wherein the memory stores executable instructions that in response to execution by the processor cause the apparatus to further perform the step of:

comparing the selected ion peaks of the two-dimensional data sets across the plurality of two-dimensional data sets and aligning the selected ion peaks according to respective intensity characteristics across the two-dimensional data sets.

35. An apparatus according to claim 27, wherein determining an area associated with the selected ion peak for each of the two-dimensional data sets further comprises determining an area associated with the selected ion peak for each of the two-dimensional data sets in association with a percent relative standard deviation.

36. An apparatus according to claim 27, wherein determining a selected ion peak in each of a plurality of two-dimensional data sets further comprises:

identifying a plurality of candidate intensity peaks in each of the two-dimensional data sets;

comparing the candidate intensity peaks across the plurality of two-dimensional data sets; and selecting one of the candidate intensity peaks evident across the plurality of two-dimensional data sets, and corresponding to a recognized compound in a compound database, as the selected ion peak.

37. An apparatus for analyzing data obtained from a component separation and mass spectrometer system, the apparatus comprising a processor and a memory storing executable instructions that, in response to execution by the processor, cause the apparatus to at least perform the steps of:

determining a selected ion peak in each of a plurality of two-dimensional data sets, each of the two-dimensional data sets being determined from a respective three-dimensional data set including data obtained from the component separation and mass spectrometer system, for each of a plurality of samples;

determining an area associated with the selected ion peak, using one of a plurality of integration procedures, for each of the two-dimensional data sets;

determining an identity of a first sample component associated with the selected ion peaks of the two-dimensional data sets, the area of each selected ion peak associated with the first sample component further corresponding to a relative quantity of the first sample component in the respective sample;

comparing the selected ion peaks across the plurality of two-dimensional data sets to determine whether a predetermined one of integration procedures was used to determine the area associated with the first sample component of a first portion of the selected ion peaks of the two-dimensional data sets, the first portion of the selected ion peaks of the two-dimensional data sets indicating a second sample component associated therewith in addition to the first sample component, the predetermined one of the integration procedures used to determine the area of each selected ion peak of the first portion associated with the first sample component comprising a first sample component mask integration procedure;

determining, if the predetermined one of integration procedures was used to determine the area associated with the first sample component of the first portion of the selected ion peaks, an area of each selected ion peak, corresponding to a relative quantity of the second sample component, for the first portion of the selected ion peaks of the two-dimensional data sets, using a second sample component mask integration procedure; and applying the first and second sample component mask integration procedures to the selected ion peaks of a second portion of the two-dimensional data sets, the second portion of the two-dimensional data sets previously having the areas of the selected ion peaks thereof determined by one of the integration procedures other than the first sample component mask integration procedure, so as to adjust the relative quantities of the first and second sample components determined to be in the samples corresponding to the second portion of the two-dimensional data sets with respect to the relative quantities of the first and second sample components determined to be in the samples corresponding to the first portion of the two-dimensional data sets.

38. An apparatus according to claim 37, wherein the memory stores executable instructions that, in response to execution by the processor, cause the apparatus to further perform the steps of:

comparing, if the predetermined one of integration procedures was not used to determine the area associated with the first sample component of a first portion of the selected ion peaks, the selected ion peaks across the plurality of two-dimensional data sets to determine the one of the integration procedures used to determine the area of each selected ion peak for an identified portion of the two-dimensional data sets, the determined one of the integration procedures comprising a template integration procedure; and applying the template integration procedure to the selected ion peaks of a remainder portion of the two-dimensional data sets, the remainder portion of the two-dimensional data sets previously having the areas of the selected ion peaks thereof determined by one of the integration procedures other than the template integration procedure, to adjust the relative quantity of the sample component determined to be in the samples corresponding to the remainder portion of the two-dimensional data sets with respect to the relative quantity of the sample component determined to be in the samples corresponding to the identified portion of the two-dimensional data sets.

39. An apparatus according to claim 37, wherein the two-dimensional data sets are configured to indicate a sample property in one dimension versus an intensity of a selected value of another sample property in the other dimension, and determining an area associated with the selected ion peak, further comprises:

determining an intensity peak origin and an intensity peak terminus in the sample property dimension;

determining a relation of each of the intensity peak origin and the intensity peak terminus with respect to a baseline intensity in the intensity dimension; and integrating the selected ion peak between the intensity peak origin and the intensity peak terminus in the sample property dimension, with respect to the relations thereof to the baseline intensity in the intensity dimension, so as to determine the area associated with the selected ion peak.

40. An apparatus according to claim 39, wherein determining an intensity peak origin and an intensity peak terminus in the sample property dimension further comprises determining an intensity peak origin and an intensity peak terminus in a time dimension.

41. An apparatus according to claim 39, wherein determining a relation of each of the intensity peak origin and the intensity peak terminus with respect to a baseline intensity in the intensity dimension further comprises at least one of:

determining whether either of the intensity peak origin and the intensity peak terminus corresponds to the baseline intensity; and determining whether either of the intensity peak origin and the intensity peak terminus is spaced apart from the baseline intensity.

42. An apparatus according to claim 41, wherein the memory stores executable instructions that, in response to execution by the processor, cause the apparatus to further perform the step of:

determining the one of the plurality of integration procedures used to determine the area associated with the selected ion peak for each of the two-dimensional data sets, according to a combination of the determined relation of the intensity peak origin to the baseline intensity and the determined relation of the intensity peak terminus to the baseline intensity.

43. An apparatus according to claim 37, wherein the memory stores executable instructions that in response to execution by the processor cause the apparatus to further perform the step of:

determining each of the two-dimensional data sets from a respective three-dimensional data set for each of a plurality of samples, each three-dimensional data set comprising a sample component mass dimension, an intensity dimension, and a time dimension.

44. An apparatus according to claim 43, wherein determining a selected ion peak in each of a plurality of two-dimensional data sets including data obtained from a component separation and mass spectrometer system further comprises determining a selected ion peak in each of a plurality of two-dimensional sets, with each two dimensional data set comprising the time dimension and the intensity dimension, for a selected sample component mass in the sample component mass dimension of the corresponding three-dimensional data set.

45. An apparatus according to claim 43, wherein the memory stores executable instructions that in response to execution by the processor cause the apparatus to further perform the step of:
- comparing the selected ion peaks of the two-dimensional data sets across the plurality of two-dimensional data sets and aligning the selected ion peaks according to respective intensity characteristics across the two-dimensional data sets.

46. An apparatus according to claim 37, wherein determining an area associated with the selected ion peak for each of the two-dimensional data sets further comprises determining an area associated with the selected ion peak for each of the two-dimensional data sets in association with a percent relative standard deviation.

47. An apparatus according to claim 37, wherein determining a selected ion peak in each of a plurality of two-dimensional data sets further comprises:
- identifying a plurality of candidate intensity peaks in each of the two-dimensional data sets;
- comparing the candidate intensity peaks across the plurality of two-dimensional data sets; and
- selecting one of the candidate intensity peaks evident across the plurality of two-dimensional data sets, and corresponding to a recognized compound in a compound database, as the selected ion peak.

48. An apparatus according to claim 37, wherein comparing the selected ion peaks across the plurality of two-dimensional data sets, further comprises comparing the selected ion peaks across the plurality of two-dimensional data sets to determine whether any of the areas thereof associated with the first sample component were determined by the predetermined one of the integration procedures, indicative of a shoulder peak in addition to a primary peak, corresponding to the second sample component in addition to the first sample component, the selected ion peaks having the areas thereof associated with the first sample component determined by the predetermined one of the integration procedures comprising the first portion of the selected ion peaks of the two-dimensional data sets.

49. An apparatus according to claim 48, wherein the memory stores executable instructions that, in response to execution by the processor, cause the apparatus to further perform the step of:
- determining a primary peak, a shoulder peak, and a peak transition therebetween, for each of the selected ion peaks comprising the first portion of the selected ion peaks of the two-dimensional data sets indicating the second sample component in addition to the first sample component.

50. An apparatus according to claim 49, wherein the memory stores executable instructions that, in response to execution by the processor, cause the apparatus to further perform the step of:
- determining an identity of the second sample component associated with the shoulder peaks of the first portion of the selected ion peaks of the two-dimensional data sets.

51. An apparatus according to claim 50, wherein the memory stores executable instructions that, in response to execution by the processor, cause the apparatus to further perform the step of:
- comparing the first sample component mask integration procedure to the second sample component mask integration procedure so as to determine a representative peak transition in the sample property dimension between the primary peak and the shoulder peak, and a representative baseline intensity in the intensity dimension.

52. An apparatus according to claim 51, wherein applying the first and second sample component mask integration procedures to the selected ion peaks of a second portion of the two-dimensional data sets, further comprises:
- executing the first sample component mask integration procedure with respect to the second portion of selected ion peaks, using the intensity peak origin and the representative peak transition in the sample property dimension with respect to the representative baseline intensity in the intensity dimension, to determine the area of the selected ion peaks of the second portion associated with the first sample component; and
- executing the second sample component mask integration procedure with respect to the second portion of selected ion peaks, using the representative peak transition and the intensity peak terminus in the sample property dimension with respect to the representative baseline intensity in the intensity dimension, to determine the area of the selected ion peaks of the second portion associated with the first sample component.

* * * * *